United States Patent
Shukla et al.

(10) Patent No.: US 9,772,552 B2
(45) Date of Patent: *Sep. 26, 2017

(54) THIOSULFATE POLYMER COMPOSITIONS AND ARTICLES

(71) Applicant: Eastman Kodak Company, Rochester, NY (US)

(72) Inventors: Deepak Shukla, Webster, NY (US); Mark R. Mis, Rush, NY (US); Dianne Marie Meyer, Hilton, NY (US)

(73) Assignee: EASTMAN KODAK COMPANY, Rochester, NY (US)

( * ) Notice: Subject to any disclaimer, the term of this patent is extended or adjusted under 35 U.S.C. 154(b) by 196 days.

This patent is subject to a terminal disclaimer.

(21) Appl. No.: 14/158,883

(22) Filed: Jan. 20, 2014

(65) Prior Publication Data

US 2014/0287349 A1    Sep. 25, 2014

Related U.S. Application Data

(63) Continuation-in-part of application No. 13/846,985, filed on Mar. 19, 2013, now abandoned.

(51) Int. Cl.

| | | |
|---|---|---|
| *C08F 228/02* | (2006.01) |
| *G03F 7/038* | (2006.01) |
| *C08F 2/50* | (2006.01) |
| *C08F 212/04* | (2006.01) |
| *A61Q 5/04* | (2006.01) |
| *A61Q 5/06* | (2006.01) |
| *A61K 8/81* | (2006.01) |
| *G03F 7/004* | (2006.01) |
| *C08F 222/40* | (2006.01) |
| *C08F 222/04* | (2006.01) |
| *C08F 226/12* | (2006.01) |
| *C08F 220/66* | (2006.01) |
| *C09D 4/00* | (2006.01) |
| *C08F 212/14* | (2006.01) |
| *C08F 232/08* | (2006.01) |
| *C08F 20/70* | (2006.01) |

(52) U.S. Cl.
CPC .......... *G03F 7/038* (2013.01); *A61K 8/81* (2013.01); *A61K 8/8147* (2013.01); *A61Q 5/04* (2013.01); *A61Q 5/06* (2013.01); *C08F 2/50* (2013.01); *C08F 212/04* (2013.01); *C08F 228/02* (2013.01); *G03F 7/0045* (2013.01); *C08F 20/70* (2013.01); *C08F 212/14* (2013.01); *C08F 220/66* (2013.01); *C08F 222/04* (2013.01); *C08F 222/40* (2013.01); *C08F 226/12* (2013.01); *C08F 232/08* (2013.01); *C08F 2222/402* (2013.01); *C08F 2222/404* (2013.01); *C08F 2222/406* (2013.01); *C08F 2222/408* (2013.01); *C09D 4/00* (2013.01); *Y02P 20/582* (2015.11)

(58) Field of Classification Search
CPC .......... C09D 4/00; C08F 20/70; C08F 228/02; C08F 212/14; C08F 220/66; C08F 2222/402; C08F 2222/404; C08F 2222/406; C08F 2222/408; C08F 226/12; C08F 232/08; G03F 7/038

See application file for complete search history.

(56) References Cited

U.S. PATENT DOCUMENTS

| | | | |
|---|---|---|---|
| 5,071,641 A | 12/1991 | Lewis | |
| 5,424,062 A | 6/1995 | Schwan et al. | |
| 5,985,514 A | 11/1999 | Zheng et al. | |
| 6,388,039 B1 | 5/2002 | Jung et al. | |
| 6,410,202 B1 * | 6/2002 | Fleming | B41C 1/1041 430/270.1 |
| 6,420,505 B1 | 7/2002 | Blevins et al. | |
| 6,465,152 B1 | 10/2002 | DoMinh et al. | |
| 6,579,662 B1 * | 6/2003 | Zheng | B41C 1/1041 101/453 |
| 6,846,608 B2 * | 1/2005 | Zheng | B41C 1/1016 430/171 |
| 7,226,722 B1 | 6/2007 | Knight | |
| 8,916,336 B2 * | 12/2014 | Shukla | B82Y 30/00 430/311 |
| 8,986,924 B2 * | 3/2015 | Shukla | G03F 7/265 430/311 |
| 9,005,878 B2 * | 4/2015 | Shukla | G03F 7/30 430/270.1 |
| 2003/0124317 A1 | 7/2003 | Zheng et al. | |
| 2005/0095390 A1 * | 5/2005 | Dinnocenzo | B82Y 10/00 428/64.4 |

FOREIGN PATENT DOCUMENTS

| | | |
|---|---|---|
| GB | 1 489 551 A | 10/1977 |
| WO | WO 2007/073482 A2 | 6/2007 |

OTHER PUBLICATIONS

Hoyle et al., "Characterization of a Thiosulfate Functionalized Polymer," 1989 American Chemical Society, pp. 280-302.

* cited by examiner

*Primary Examiner* — Ling Choi
*Assistant Examiner* — David L Miller
(74) *Attorney, Agent, or Firm* — J. Lanny Tucker

(57) ABSTRACT

A thiosulfate polymer composition includes an electron-accepting photosensitizer component, either as a separate compound or as an attachment to the thiosulfate polymer. The thiosulfate polymer composition can be applied to various articles, or used to form a predetermined polymeric pattern after photothermal reaction to form crosslinked disulfide bonds, removing non-crosslinked polymer, and reaction with a disulfide-reactive material. Such thiosulfate polymer compositions can also be used to sequester metals in nanoparticulate form, and as a way for shaping human hair in hairdressing operations.

18 Claims, No Drawings

THIOSULFATE POLYMER COMPOSITIONS AND ARTICLES

RELATED APPLICATIONS

This is a Continuation-in-part application of U.S. Ser. No. 13/846,985 (now abandoned) filed on Mar. 19, 2013 by Shukla, Mis, and Meyer that is incorporated herein by reference in its entirety.

U.S. Ser. No. 14/158,884 filed on Jan. 20, 2014 (and issued as U.S. Pat. No. 9,005,878 on Apr. 14.2015) , by Shukla, Donovan, and Mis, which is a Continuation-in-part application of U.S. Ser. No. 13/847,031 (now abandoned), filed on Mar. 19, 2013.

U.S. Ser. No. 14/158,890 filed on Jan. 20, 2014 (and issued as U.S. Pat. No. 8,986,924 on Mar. 24, 2015), by Shukla and Donovan, which is a Continuation-in-part application of U.S. Ser. No. 13/847,049 (now abandoned), filed on Mar. 19, 2013.

U.S. Ser. No. 14/158,897 filed on Jan. 20, 2014., by Mis and Shukla, which is a Continuation-in-part application of U.S. Ser. No. 13/847,063 (now abandoned), filed on Mar. 19, 2013.

U.S. Ser. No. 14/158,902 filed on Jan. 20, 2014 (and issued as U.S. Pat. No. 8,916,336 on Dec. 23, 2014), by Shukla, Donovan, and Dirmyer, which is a Continuation-in-part application of U.S. Ser. No. 13/847,083 (now abandoned), filed on Mar. 19, 2013.

FIELD OF THE INVENTION

This invention relates to polymers having thiosulfate groups, photosensitive compositions containing the polymers, and methods for using the polymers including methods for providing patterns. More particularly, the present invention provides photosensitive compositions useful in photolithographic patterning methods.

BACKGROUND OF THE INVENTION

Alkylthiosulfates (R—S—$SO_3^-Na^+$), known as Bunte salts, have been known for a long time [Bunte, H. *Chem. Bet.* 1874, 7, 646]. These salts are readily prepared by reacting alkylhalides with sodium thiosulfate. Extensive reviews on the preparation and classical reactions of Bunte salts have appeared in the literature (for example, Milligan, B.; Swan, J. M. *Rev. Pure Appl. Chem.* 1962, 12, 72).

Much of the useful chemistry of Bunte salts results from the potential of the sulfite moiety to leave the molecule. Small molecule Bunte salts have various uses. For instance they can be used as insecticides or fungicides, radiation protecting agents (for example as described in U.S. Pat. No. 5,427,868 of Bringley et al.), and paint additives.

Polymeric Bunte salts and Bunte salt derivatives have been used for setting hair as described in U.S. Pat. No. 5,071,641 (Lewis) and U.S. Pat. No. 5,424,062 (Schwan et al.).

Water-soluble polymers formed from thiosulfate salts are useful in a variety of applications including their use to crosslink or otherwise modify the properties of natural materials such as wool fibers, cellulosic fibers, and leathers, and as water-insoluble polymeric sulfur dyes. These water-soluble polymers are also used in the coating industry.

Bunte salts are commonly reduced to corresponding thiols either by decomposition with mineral acids or by treatment with reducing agents such as $NaBH_4$, dithioerythritol, or mercaptoethanol. In addition, Bunte salts can be decomposed to disulfides at moderate temperatures. In solid state, Bunte salts are known to decompose upon heating to form disulfides, a feature that has been used as thermally switchable imaging materials in printing plates. By "switchable" is meant that the polymer is rendered from hydrophilic to relatively more hydrophobic, or from hydrophilic to relatively more hydrophobic, upon exposure to heat. For example, U.S. Pat. No. 5,985,514 (Zheng et al.) and U.S. Pat. No. 6,465,152 (DoMinh et al.) describe lithographic printing plate precursors that are composed of thiosulfate containing polymers, which upon exposure to IR radiation are crosslink as the thiosulfate groups are decomposed.

Bunte salts can be used to synthesize disulfides by oxidation [Affleck, J. G.; Dougherty, G. J. *Org. Chem.* 1950, 15, 865. and Milligan, B. L.; Swan, L. M. *J. Chem. Soc.* 1962, 2172], acidic hydrolysis [Kice, J. L. *J. Org. Chem.* 1963, 28, 957], or alkaline degradation [Alonso, M. E.; Aragona, H. *Org. Synth.* 1978, 58, 147]. Disulfides also can be formed from Bunte salts electrochemically [Czerwinski, A.; Orzeszko, A.; Kazimierczuk, Z.; Marassi, R.; Zamponi, S. *Anal. Lett.* 1997, 30, 2391]. This method has been extended to form polydisulfides from "double" Bunte salts, that is, molecules carrying two thiosulfate groups, using electrochemistry with gold electrodes [Nann, T.; Urban, G. A. *J. Electroanal. Chem.*, 2001, 505, 125].

In all these noted methods, the Bunte salts are either decomposed by heating or electrochemically in solution, or at high pH. No efficient photochemical method to decompose Bunte salts is known. More specifically, a simple method for patterning thin films using Bunte salt polymers is not known and would be desirable for various purposes.

It would be very desirable to decompose Bunte salts by photochemical means, or by using a photochemical electron transfer process (also known as photoinduced electron transfer).

SUMMARY OF THE INVENTION

This invention provides composition comprising a thiosulfate polymer and an electron-accepting photosensitizer component, provided that when the electron-accepting photosensitizer component is not covalently attached to the thiosulfate polymer, it has a spectral absorption of less than 750 nm.

In other compositions of this invention, a thiosulfate (Bunte salt) composition comprises:

a thiosulfate copolymer comprising an electron-accepting photosensitizer component, an ionomer, and a thiosulfate group as a side chain, which thiosulfate copolymer is capable of undergoing a chemical transformation upon single electron oxidation upon photoexposure, thus causing a change in solubility of the copolymer when photoexposed, and a tetraalkyl ammonium ion.

This invention also provides an article comprising a substrate having a coating comprising any embodiment of the composition of this invention.

Some embodiments of this invention comprises a non-crosslinked polymer comprising, in random order, (a) recurring units comprising pendant thiosulfate groups, and (b) recurring units comprising an electron-accepting photosensitizer component covalently attached to the polymer backbone. Such non-crosslinked polymer can be used in the compositions and methods of this invention, but the compositions and methods of this invention can be used with different thiosulfate polymers.

In still other embodiments, a polymer comprises recurring units comprising pendant groups comprising both an electron-accepting photosensitizer component group and a thiosulfate group. Such polymers can also comprise additional recurring units that do not contain thiosulfate groups or electron-accepting photosensitizer groups.

In addition, the present invention provides a method of forming a pattern in a polymeric composition, the method comprising:
  providing a polymeric layer comprising a non-crosslinked thiosulfate polymer,
  photochemically reacting the non-crosslinked thiosulfate polymer to provide a crosslinked polymer having disulfide groups in a predetermined pattern in the polymeric layer, leaving non-crosslinked thiosulfate polymer in area(s) outside of the predetermined pattern,
  optionally washing the polymeric layer to remove the non-crosslinked thiosulfate polymer while leaving the crosslinked polymer in the predetermined pattern, and either:
    (i) treating the crosslinked polymer with a disulfide-reactive material, or
    (ii) when the polymeric layer further comprises a redox active metal ion, treating the predetermined pattern with a metal ion that is capable of reacting with the redox active metal ion.

Other embodiments of this invention comprise a method of sequestering metal in a polymeric composition, the method comprising:
  providing a polymeric layer comprising a non-crosslinked thiosulfate polymer that also comprises pendant organic charged groups,
  photochemically reacting the non-crosslinked thiosulfate polymer to provide polymeric layer areas comprising a crosslinked polymer having disulfide groups in a predetermined pattern in the polymeric layer, and polymer layer areas outside the predetermined pattern comprising non-crosslinked thiosulfate polymer,
  optionally washing the polymeric layer to remove the non-crosslinked thiosulfate polymer, while leaving the crosslinked polymer in the predetermined pattern,
  treating the polymeric layer with a metal ion solution to incorporate ions of a metal in the predetermined pattern comprising the crosslinked polymer having disulfide groups,
  converting the incorporated metal ions to metal nanoparticles of the corresponding metal, and
  electrolessly plating the metal nanoparticles to obtain a coating of the metal.

Still another embodiment of this invention comprises a method for sequestering metal ion in a polymeric composition, the method comprising:
  providing a polymeric layer comprising a non-crosslinked thiosulfate polymer and a redox active metal ion,
  photochemically reacting the thiosulfate polymer to provide polymeric layer areas comprising a crosslinked polymer having disulfide groups in a predetermined pattern in the polymeric layer, and also to provide polymeric layer areas outside the predetermined pattern comprising non-crosslinked thiosulfate polymer,
  optionally washing the polymeric layer to remove the non-crosslinked thiosulfate polymer in the polymeric layer areas outside the predetermined pattern,
  contacting the polymeric layer with a metal ion solution to carry out a redox reaction and to incorporate metal nanoparticles on the areas comprising the crosslinked polymer, and
  electrolessly plating the metal nanoparticles to obtain a predetermined pattern of the metal nanoparticles.

In addition, a method of this invention comprises:
  providing a polymeric layer comprising a non-crosslinked thiosulfate polymer that also comprises pendant electron-accepting photosensitizer groups,
  photochemically reacting the non-crosslinked thiosulfate polymer to provide polymeric layer areas comprising a crosslinked polymer having disulfide groups in the polymeric layer,
  optionally washing the polymeric layer to remove any non-crosslinked thiosulfate polymer while leaving the crosslinked polymer having disulfide groups in the polymeric layer, and
  contacting the polymeric layer with a dispersion of metal nanoparticles to adhere the metal nanoparticles to the crosslinked polymer having disulfide groups.

In another embodiment of this invention, a method of forming a pattern in a polymeric composition, comprises:
  providing a polymeric layer or a nonpolymeric layer comprising an electron-accepting photosensitizer component,
  providing a polymeric layer comprising a non-crosslinked thiosulfate polymer adjacent to the polymeric layer or nonpolymeric layer comprising the electron-accepting photosensitizer component,
  photochemically reacting the non-crosslinked thiosulfate polymer to provide a crosslinked polymer having disulfide groups in a predetermined pattern in the polymeric layer, leaving non-crosslinked thiosulfate polymer in area(s) outside of the predetermined pattern,
  optionally washing the polymeric layer to remove the non-crosslinked thiosulfate polymer while leaving the crosslinked polymer having disulfide groups in the predetermined pattern, and
  treating the crosslinked polymer having disulfide groups with a disulfide-reactive material.

The present invention provides a novel thiosulfate polymer, thiosulfate polymer-containing composition and method for decomposing polymeric Bunte salts (thiosulfate polymers) by photochemical electron transfer means. For example, the present invention can be used to provide patterns by decomposing polymeric Bunte salts using a photochemical electron transfer (also called photoinduced electron transfer) process. In addition, the present invention can be used to provide negative working photoresists comprising a Bunte salt polymer and a photoactivated electron acceptor, and the surface energy of the photoresist can be modified. Other methods of the present invention can be used to obtain conductive or non-conductive metal coatings after photochemical reaction of the thiosulfate polymers.

Many advantages of this invention are achieved using polymeric Bunte salts in the presence of electron-accepting photosensitizer components. In some embodiments, the electron-accepting photosensitizer components are separate compounds used in mixture with the thiosulfate polymers, while in other embodiments, the electron-accepting photosensitizer components are covalently attached to the thiosulfate polymers. The electron-accepting photosensitizer components can be selected to provide sensitivity to any desired spectral absorption.

Most compositions of this invention are light sensitive and can provide light sensitive imaging layers, which when exposed to actinic radiation (generally less than 750 nm) the exposed regions are rendered insoluble, thereby providing a pattern that can be used for a variety of purposes such as surface energy modulation or electroless metal plating.

The present invention provides at least the following advantages:

1. This invention involves a photo-initiated electron transfer reaction in a solid thiosulfate polymer that creates changes in the solubility of the material. Because the invention relies on photo-initiated electron transfer rather than thermal decomposition, resolution of resulting patterns is much greater.

2. The thiosulfate polymer composition of this invention includes a stable thiosulfate polymer that can be conveniently fabricated into films, slabs, discs, and other solid forms. In addition, the thiosulfate polymers can be incorporated into porous or non-porous polymeric particles and such particles can be provided and used as dispersions or emulsions, or provided as coatings.

3. The solubility changes in the thiosulfate polymer composition of the invention are large, permanent, localized, and can easily be detected, forming the basis for patterning.

4. In some embodiments, covalent attachment of the electron-accepting photosensitizer component to a thiosulfate polymer backbone (as opposed to simply dissolving the component in the thiosulfate polymer to form a solid solution) allows for the incorporation of much higher effective concentration of such electron-accepting photosensitizer components without problems associated with phase separation such as crystallization. Higher concentrations of the electron-accepting photosensitizer component lead to desirable increases in changes in photochemical sensitivity, thereby improving the performance of the thiosulfate polymer composition and resulting coatings. In addition, the permanence of recorded information in the resulting patterns is improved due to low mobility of high molecular weight structures.

5. Coatings of the thiosulfate polymer compositions of this invention can be used to modulate surface characteristics such as changing part (pattern) or all of a surface from a hydrophilic nature to a hydrophobic nature.

One purpose of the present invention is to provide a photosensitive resin composition, which after exposure to light, undergoes a reaction that generates organic functionalities that could be used for absorption of various metals. These resulting metal centers are suitable for electroless metal plating. Thus, the present invention provides for the formation of a conducting layer selectively on a resin pattern by coating the thiosulfate polymer composition on a substrate, followed by exposure to suitable radiation, development, and deposition of metal nanoparticles or wires. By using the method of this invention, a conductive layer with a high adhesive strength, which can be similar to the adhesive strength obtained through sputtering, can be obtained at a low cost through large-scale production.

Compared to known electroless metal plating processes, the method of this invention is very simple and does not require complicated monitoring and management of all agents. In addition, the method of this invention does not require a pilot line and the thiosulfate polymer composition layer can be formed on the substrate through a stable process suitable for large-scale production.

For example, in some embodiments the present invention provides a capability of adsorbing fine metal nanowires and nanoparticles onto a patterned area.

The present invention can be used to provide letterpress printing plates, flexographic printing plates, offset printing plates, graphic arts films, proofing materials, photoresists, circuit board resists, and stereolithographic materials. In addition, the thiosulfate polymers described herein can be used as ionomers in fuel cells.

DETAILED DESCRIPTION OF THE INVENTION

Definitions

As used herein to define various components of the compositions and layers, unless otherwise indicated, the singular forms "a", "an", and "the" are intended to include one or more of the components (that is, including plurality referents).

Each term that is not explicitly defined in the present application is to be understood to have a meaning that is commonly accepted by those skilled in the art. If the construction of a term would render it meaningless or essentially meaningless in its context, the term definition should be taken from a standard dictionary.

The use of numerical values in the various ranges specified herein, unless otherwise expressly indicated otherwise, are considered to be approximations as though the minimum and maximum values within the stated ranges were both preceded by the word "about". In this manner, slight variations above and below the stated ranges can be used to achieve substantially the same results as the values within the ranges. In addition, the disclosure of these ranges is intended as a continuous range including every value between the minimum and maximum values.

Under otherwise indicated herein, the terms "polymer", "thiosulfate polymer", "polymer having thiosulfate groups", "polymer having Bunte salt moieties", and "Bunte salt polymer" are considered to be the same in the description of the present invention.

A "thiosulfate" group is a substituent defined by the following Structure I.

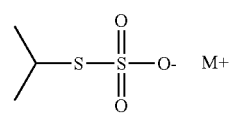

Any compound bearing this thiosulfate group is called a "thiosulfate compound." When the thiosulfate group is attached to an organic moiety, the resulting compound is an "organic thiosulfate" or Bunte salt. If this organic thiosulfate is a polymer (having a molecular weight of at least 1,000), the compound is considered a thiosulfate polymer.

Unless otherwise indicated herein, the terms "composition", "thiosulfate polymer composition", and "thiosulfate polymer containing composition" are intended to be the same in the description of the present invention.

Thiosulfate Polymers

In their simplest form, the thiosulfate polymers used in the present invention can be generally represented by the formula R—S—SO$_3$M, wherein R represents a suitable polymeric backbone, and M is a suitable cation.

When R is a polymer backbone, it can have multiple —S—SO$_3$M groups distributed randomly or in blocks of recurring units along the chain of atoms forming the polymer backbone. Useful polymers that provide the backbone are described in most detail below. The thiosulfate polymers can be formed as vinyl polymers from ethylenically unsaturated polymerizable monomers using or emulsion or suspension polymerization techniques, or they can be condensation polymers formed using appropriate reactive precursor compounds (for example diols with diacids to form polyester or diamines with diols to form polyamides).

In addition, the thiosulfate polymers described in U.S. Pat. No. 5,424,062 (noted above) can be used in the practice of this invention, and this disclosure is incorporate herein by reference.

M is hydrogen or a suitable monovalent cation such as a metal cation or an organic cation including but not limited to, an alkali metal ion (lithium, sodium, potassium, and cesium), ammonium, pyridinium, morpholinium, benzolium, imidazolium, alkoxypyridinium, thiazolium, and quinolinium cations. Divalent cations can be present in small amounts so that premature crosslinking of the thiosulfate polymer is minimized. Thus, in most embodiments, M is a monovalent cation such as potassium ion or sodium ion.

Any polymer containing one or more thiosulfate moieties can be used in the present invention. For example, suitable polymers include but are not limited to, vinyl polymers derived at least in part from methacrylate or acrylate ethylenically unsaturated polymerizable monomers (known herein as "polymethacrylates" and "polyacrylates", including both homopolymers and copolymers), polyethers, poly(vinyl ester)s, and polystyrenes (including homopolymers and copolymers derived from styrene and styrene derivatives having one or more substituents on the pendant benzene ring or attached along the polymer backbone). Such thiosulfate polymers have an entirely carbon backbone. However, pendant thiosulfate groups can be incorporated into condensation polymers including but not limited to, polyesters, polyamides, polyurethanes, polycarbonates, polymers derived from cellulose esters, and polysiloxanes using chemistry that would be readily known to one skilled in the art.

All of the thiosulfate polymers described herein can be mixed with an electron-accepting photosensitizer component, or such an electron-accepting photosensitizer component can be incorporated into the thiosulfate polymer so that the thiosulfate polymer includes both types of pendant groups (thiosulfate groups and electron-accepting photosensitizer components). In addition, the thiosulfate polymers can be designed so that the same recurring units comprise pendant groups that comprise both electron-accepting photosensitizer groups and thiosulfate groups.

In general, useful thiosulfate polymers are optically transparent in the spectral region where the electron-accepting photosensitizer component absorbs. That is, the thiosulfate polymer should not have significant absorption at the excitation wavelengths, and should not interfere with the chemical transformation of the thiosulfate moieties. The thiosulfate polymers can be linear, branched, or dendritic in form.

Useful thiosulfate polymers generally have a molecular weight ($M_n$) of at least 1,000 and up to and including 1,000,000, or typically at least 10,000 and up to and including 100,000, as determined using size exclusion chromatography (SEC).

Useful thiosulfate polymers can also have a glass transition temperature ($T_g$) of at least 20° C. and up to and including 250° C. or at least 50° C. and up to and including 150° C., as determined using Differential Scanning calorimetry (DSC).

In such polymers, a thiosulfate group or moiety can be represented by the following Structure II:

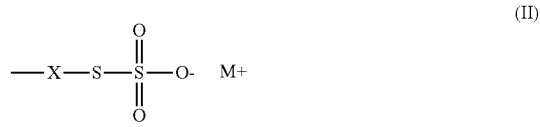

wherein X is a suitable divalent linking group that is attached to a polymer backbone, and M is a cation as defined above.

Useful X divalent linking groups in Structure (II) include but are not limited to, —(COO)$_n$—(Z)$_m$— wherein n is 0 or 1 and m is 0 or 1. Z can be a substituted or unsubstituted divalent aliphatic group having 1 to 6 carbon atoms including alkylene groups (such as methylene, ethylene, n-propylene, isopropylene, butylenes, 2-hydroxypropylene and 2-hydroxy-4-azahexylene), which divalent aliphatic group can comprise one or more oxygen, nitrogen or sulfur atoms in the chain (such as carbonamido, sulfonamide, alkylenecarbonyloxy, ureylene, carbonyloxy, sulfonyloxy, oxy, dioxy, thio, dithio, seleno, sulfonyl, sulfonyl, and imido), a substituted or unsubstituted arylene group having 6 to 14 carbon atoms in the aromatic ring (such as phenylene, naphthalene, anthracylene, and xylylene), a substituted or unsubstituted combination of alkylene and arylene groups such as substituted or unsubstituted arylenealkylene or alkylenearylene groups having at least 7 and to and including 20 carbon atoms in the chain (such as p-methylenephenylene, phenylenemethylenephenylene, biphenylene, and phenyleneisopropylene-phenylene), or a heterocyclic ring (such as pyridinylene, quinolinylene, thiazolinylene, and benzothioazolylene). In addition, X can be a substituted or unsubstituted alkylene group, a substituted or unsubstituted arylene group, in a substituted or unsubstituted arylenealkylene group or alkylenearylene group, having the same definitions as Z. In some embodiments, it is advantageous to covalently attach both a thiosulfate group and an electron-accepting photosensitizer group in the same pendant group in a single recurring unit. Thus, in Structure II, X can be or be derived from an electron-accepting photosensitizer component as described below.

As the thiosulfate group is generally located pendant to the polymer backbone, it can be part of an ethylenically unsaturated polymerizable monomer that can be polymerized using conventional techniques to form vinyl homopolymers of the thiosulfate-containing recurring units, or vinyl copolymers when copolymerized with one or more additional ethylenically unsaturated polymerizable monomers. A thiosulfate polymer can include more than one type of recurring unit containing thiosulfate group as described herein. For example, the thiosulfate polymers can comprise different recurring units derived from different ethylenically unsaturated polymerizable monomers. Alternatively, the thiosulfate polymer can be have the same or different backbone in each recurring unit, but comprise different thiosulfate groups as defined by different X (with different "n", "m", or Z groups) as noted above for Structure (H).

In embodiments of the thiosulfate polymers that are vinyl polymers, the thiosulfate-containing recurring units generally comprise at least 1 mol % of all recurring units in the thiosulfate polymer, or typically at least 15 mol % and up to and including 90 mol %, or even up to and including 100 mal % of all recurring units. In most embodiments, the thiosulfate-containing recurring units comprise at least 15 mol % and up to and including 50 mol % of the total recurring units in the thiosulfate polymer. For the vinyl thiosulfate polymers that are copolymers, the remaining recurring units can be derived from one or more ethylenically unsaturated polymerizable monomers including but not limited to methacrylates, acrylates, acrylamides, methacrylamides, styrene and its derivatives, vinyl ethers, vinyl esters, (meth)acrylonitrile, vinyl pyrrolidones, maleimides, vinyl imidazoles, and vinyl formamide. A skilled polymer chemist would be able to choose suitable co-monomers to be used to make desired thiosulfate copolymers within the spirit of the present invention. The amount of recurring units derived from these additional ethylenically unsaturated polymerizable monomers can be at least 10 mol % and up to and including 99 mol %, or more likely at least 20 mol % and up to and including 50 mol %, based on the total recurring units in the thiosulfate polymer. In general, in the thiosulfate polymers of this invention, the various recurring units are arranged in random order along the polymer molecule, although blocks of certain recurring units can be arranged if desired.

Thiosulfate polymers useful in the present invention can be prepared in several ways using understanding and reactants available to a skilled polymer chemist. For example, the useful thiosulfate monomers and reactive ethylenically unsaturated polymerizable co-monomers can be obtained from a number of commercial sources or readily prepared.

For example, thiosulfate-containing ethylenically unsaturated polymerizable monomers can be prepared from the reaction between an alkyl halide and thiosulfate salt as described in the seminal teaching of Bunte, *Chem. Ber.* 7, 646, 1884. Thiosulfate polymers can be prepared either from functional ethylenically unsaturated polymerizable monomers or from preformed polymers having requisite reactive groups. For example, if the functional ethylenically unsaturated polymerizable monomer is a vinyl halide polymer, the functional vinyl polymerizable monomer can be prepared as illustrated as follows:

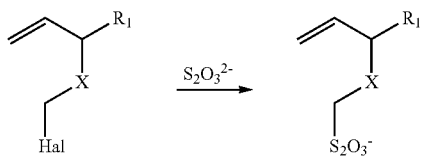

wherein $R_1$ is hydrogen or a substituted or unsubstituted alkyl group comprising 1 to 10 carbon atoms or an aryl group, Hal represents a halide, and X represents a divalent linking group as defined above. The conditions for these reactions are known in the art.

Thiosulfate polymers can also be prepared from preformed polymers in a similar manner as described in U.S. Pat. No. 3,706,706 (Vandenberg) as illustrated as follows, the disclosure of which is incorporated herein by reference for the polymer synthetic methods:

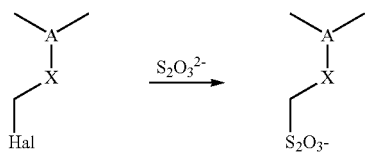

wherein A represents the polymer backbone, Hal represents a halide, and X represents a divalent linking group as described above.

In addition, thiosulfate polymers can be prepared using the reaction of an alkyl epoxide (on a preformed polymer or a functional monomer) with a thiosulfate salt, or between an alkyl epoxide (on a preformed polymer of a functional monomer) and a molecular containing a thiosulfate moiety (such as 2-aminoethanethiosulfuric acid), as illustrated by Thames, *Surf. Coating*, 3 (*Waterborne Coat.*), Chapter 3, pp. 125-153, Wilson et al (Eds.) and as follows:

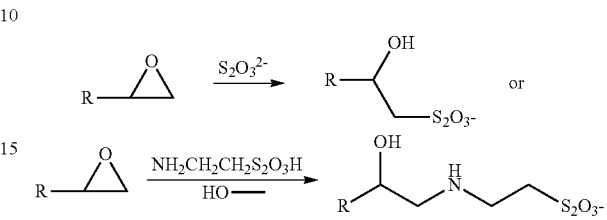

wherein R represents a substituted or unsubstituted alkyl or aryl groups. The conditions for these reactions are known in the art and require only routine experimentation to complete.

In some other embodiments of this invention, the thiosulfate polymer compositions of this invention comprise a thiosulfate polymer that further comprises an electron-accepting photosensitizer component that is a covalently-connected component. In other words, the electron-accepting photosensitizer component is another group that is incorporated within the thiosulfate polymer, for example as a pendant group connected to the polymer backbone using a suitable linking group, in some recurring units of the thiosulfate polymer.

For example, useful linking groups can be any aliphatic or hydrocarbon linking group that does not adversely affect the usefulness of the thiosulfate polymer. Such linking groups include but are not limited to, $-(COO)_n(Z)_m-$ wherein n is 0 or 1, m is 0 or 1, and Z is a substituted or unsubstituted alkylene group having 1 to 6 carbon atoms (such as methylene, ethylene, n-propylene, isopropylene, butylenes, 2-hydroxypropylene and 2-hydroxy-4-azahexylene) that can have one or more oxygen, nitrogen or sulfur atoms in the chain, carbonamido [$-C(=O)-NH-$], sulfonamide [$-SO_2-NH-$], a substituted or unsubstituted arylene group having 6 to 14 carbon atoms in the aromatic ring (such as phenylene, naphthalene, anthracylene and xylylene), or a substituted or unsubstituted arylenealkylene (or alkylenearylene) group having 7 to 20 carbon atoms in the chain (such as p-methylenephenylene, phenylenemethylenephenylene, biphenylene and phenyleneisopropylene-phenylene). In addition, the linking group can be an alkylene group, an arylene group, vinylenecarbonyloxy [$-CR=CR'-C(=O)-O-$] wherein R and R' are independent hydrogen, methyl, or ethyl, acetylimino [$CH_3C(=O)-N<$], alkylenecarbonyloxy [for example, $-CH=CH-CH_2-C(=O)-O-$], alkyleneimino (for example, $-CH_2-NH-$), alkylenecarbonyloxy [for example, $-CH_2-C(=O)-O-$], benzylene, carbonyldioxy diazo [$-N=N-$], and ureylene [$-NH-C(=O)-NH-$].

For example, the linking group can be a substituted or unsubstituted divalent organic linking group that can have least one oxygen, sulfur, or nitrogen heteroatom in the organic linking group chain. For example, useful Z groups include but are not limited to, carbonyloxy [$-C(=O)-O-$], sulfonyloxy [$-SO_2-O-$], oxy ($-O-$), dioxy ($-O-O-$) thio ($-S-$), dithio ($-S-S-$), seleno ($-Se-$), sulfinyl ($-SO-$), sulfonyl ($-SO_2-$), carbonamido [—C(=O)—NH—], sulfonamide [—SO$_2$—NH—], substituted or unsubstituted arylene (such as substituted or unsubstituted phenylene), substituted or unsubstituted cycloalkylene having 5 to 8 carbon atoms in the chain (such as pentylene, 1,3-hexylene, 1,4-hexylene, and 3-methyl-1,4-hexylene), imido (—NH—), vinylenecarbonyloxy [—CR=CR'—C(=O)—O—] wherein R and R' are independent hydrogen, methyl, or ethyl, acetylimino [CH$_3$C(=O)—N<], alkylenecarbonyloxy [for example, —CH=CH—CH$_2$—C(=O)—O—], alkyleneimino (for example, —CH$_2$—NH—), alkylenecarbonyloxy [for example, —CH$_2$—C(=O)—O—], benzylene, carbonyldioxy [—O—C(=O)—O—], diazo [—N=N—], and ureylene [NH—C(=O)—NH—]. Combinations of two or more of the linking groups can be used to form a divalent linking group.

For example, the thiosulfate polymer can be a copolymer comprising: (a) recurring units comprising thiosulfate groups (as defined in more detail above), and (b) recurring units comprising the electron-accepting photosensitizer component that is derived from an electron-accepting photosensitizer compound, for example such as one of PS-1 through PS-28 described below.

The relative amount of the (a) and (b) recurring units can vary considerably, but in general, (a) recurring units comprise at least 1 mol % and up to and including 99.9 mol % of the total polymer recurring units, and the (b) recurring units comprise at least 0.01 mol % and up to and including 99 mol % of the total polymer recurring units. More typically, the (a) recurring units comprise at least 10 mol % and up to and including 75 mol % of the total polymer recurring units, and the (b) recurring units comprise at least 25 mol % and up to and including 90 mol % of the total polymer recurring units.

When the thiosulfate polymers are copolymers comprising both thiosulfate groups and electron-accepting photosensitizer components within the polymer molecule, such copolymers can further comprises (c) additional recurring units other than the (a) and (b) recurring units. Such (c) additional recurring units can be derived from one or more ethylenically unsaturated polymerizable monomers as described above, which would be readily apparent to a skilled worker in the art, and such (c) additional recurring units can be present in an amount of at least 0.1 mol % and up to and including 50 mol % based on the total recurring units in the thiosulfate polymer, while the (a) recurring units can be present in an amount of at least 10 mol % and up to and including 50 mol %, and the (b) recurring units can be present in an amount of at least 10 mol % and up to and including 50 mol %, all based on the total recurring units in the thiosulfate polymer.

In some embodiments, one or more of the additional (c) recurring units can comprise a pendant charged group, that is, either negative-charged and positive-charged groups. In particular embodiments, the additional (c) recurring units comprise a pendant carboxy group, carboxylate, phospho, phosphonate, phosphate, sulfo, sulfonate, or sulfite group, or combinations of such groups in the same recurring units.

In other embodiments, the (c) recurring units are present in the copolymer with the (a) and (b) recurring units, in an amount of up to 50 mol %, the (a) recurring units are present in the copolymer in an amount of at least 1 mol %, and the copolymer further comprises (d) recurring units that have a total neutral charge and are present in an amount of at least 1 mol % and up to and including 49 mol %.

In such embodiments, the molar ratio of the (a) recurring units to the (d) recurring units can be from 1:3 to 3:1.

In still other embodiments, the copolymer comprises (a) recurring units comprising thiosulfate groups and (c) recurring units that comprise a pendant charged group in an amount of at least 0.1 mol %. The (b) and (d) recurring units can be absent from such embodiments.

Thiosulfate polymers comprising electron-accepting photosensitizer components in at least some of the recurring units can be prepared by methods illustrated below using reactive components and conditions that would be readily apparent to one skilled in the art using the representative teaching provided below.

Thiosulfate Polymer Compositions

There are various ways to formulate the thiosulfate polymer compositions of the present invention.

In some embodiments, the thiosulfate polymer is thoroughly mixed with one or more electron-accepting photosensitizer components (described below) that is a compound(s) separate from the thiosulfate polymer. This separate compound(s) can be polymeric or non-polymeric. In other words, the electron-accepting compound can be a non-polymeric compound, or it can be attached to a polymer that is not a thiosulfate polymer. This mixture of thiosulfate polymer and one or more electron-accepting photosensitizer components can be supplied as a dry mixture or in solution with one or more suitable solvents, such as tetrahydrofuran (THF), acetonitrile, acetone, methyl ethyl ketone (MEK), dioxane, dimethyl acetamide (DMac), and dimethyl formamide (DMF).

The thiosulfate group is generally present in the thiosulfate polymer composition of this invention in a relatively high concentration. For example, the thiosulfate groups are present in the thiosulfate polymer(s) in the thiosulfate polymer composition to provide at least 10 mol % and up to and including 100 mol % of the recurring units of the thiosulfate polymer. In such embodiments, the electron-accepting photosensitizer component can be present in an amount of at least 0.001 weight % and up to and including 20 weight % based on the total dry weight of the thiosulfate polymer composition, for example as part of a thiosulfate polymeric layer or an article (described below), with the balance of the thiosulfate polymer composition being any optional additives (described below).

As noted above, in other embodiments, the electron-accepting photosensitizer component is covalently attached to the thiosulfate polymer so that this thiosulfate polymer has both thiosulfate groups and electron-accepting photosensitizer components attached to the polymer backbone as pendant groups or covalently connected components.

In still other embodiments, a thiosulfate polymer in solution is mixed with metal salt to create a charge transfer complex, which charge transfer complex behaves as a metal complex electron-accepting photosensitizer component in the practice of this invention.

Compounds that can be used as electron-accepting photosensitizer components include but are not limited to, metal complexes such as copper sulfate, copper nitrate, nickel chloride, nickel sulfate, zinc acetate, and others that would be readily apparent to one skilled in the art.

In many embodiments, the thiosulfate polymer composition of the present invention has a spectral absorption that is different than the spectral absorption of either the thiosulfate polymer or the metal complex electron-accepting photosensitizer component alone.

The electron-accepting photosensitizer component used in the present invention initiates the chemical transformation of the thiosulfate groups in the thiosulfate polymer in response to suitable radiation. Thus, the electron-accepting photosensitizer component must be capable of oxidizing the thiosulfate anion to a radical after the electron-accepting photosensitizer component has absorbed light (that is, photo-induced electron transfer). Thus, in some embodiments, upon absorption of appropriate actinic radiation, the electron-accepting photosensitizer component is capable of accepting an electron from the reactant thiosulfate moiety. In other embodiments of the invention, upon absorption of suitable actinic radiation, the electron-accepting photosensitizer component can be fragmented to provide an oxidant that is capable of accepting an electron from the thiosulfate group.

To determine whether a compound is capable of oxidizing the thiosulfate groups in the thiosulfate polymer to provide a radical after the compound has absorbed light, reaction energetics can be used. There are three controlling parameters in reaction energetics: (1) the excitation energy ($E_{PS*}$), (2) the reduction potential ($E_{PS}^{red}$) of the electron-acceptor photosensitizer component (PS), and (3) the oxidation potential ($E_R^{ox}$) of the reactant thiosulfate moiety (R) that is an electron donor. For these reactions to be energetically feasible, the energy of the excited state should be higher or only slightly lower than the energy stored in the primary product, the radical ion pair, $PS^{-*}R^{+*}$.

The excitation energy of the electron-accepting photosensitizer component is conveniently determined from the midpoint of the normalized absorption and emission spectrum of PS, if the reaction proceeds from the singlet excited state. However, if the reaction proceeds via the triplet state, then the triplet energy of PS should be used as the excitation energy.

The energy of the radical ion pair, $E_{IP}$, is given by the following Equation 1, wherein Δ is an energy increment that depends on the medium polarity and ranges from nearly zero in highly polar media to about 0.3 eV in the least polar media. The oxidation ($E_R^{ox}$) and reduction ($E_{PS}^{red}$) potentials are readily obtained from conventional electrochemical measurements in polar solvents such as acetonitrile or methylene chloride.

$$E_{IP} = E_R^{ox} - E_{PS}^{red} + \Delta \qquad \text{Equation 1}$$

Polymeric media tend to be low in dielectric constant, and as a result would not strongly solvate the radical ion pair. Thus, the energy increment Δ in Equation 1 is expected to be near the maximum value, that is, in the range of at least 0.2 eV and up to and including 0.3 eV. Thus, electron-accepting photosensitizer components with excitation energy equal to or larger than the difference between the oxidation potential of the reactant and the reduction potential of the acceptor, ($E_R^{ox} - E_{PS}^{red}$), will satisfy the energetic requirements of photoinitiating the reaction as described in the following Equation 2:

$$E_{PS*} \geq E_R^{ox} - E_{PS}^{red} \qquad \text{Equation 2}$$

It is more convenient to express the energetic requirements of the electron-accepting photosensitizer component relative to the donor in terms of a rearranged form of Equation 2 shown below as Equation 3:

$$E_{PS*} + E_{PS}^{red} \geq E_R^{ox} \qquad \text{Equation 3}$$

According to Equation 3, for the reaction to be energetically feasible, the algebraic sum of the excitation energy of the electron-accepting photosensitizer component and its reduction potential should be approximately equal to or larger than the oxidation potential of the reactant. When the reactant is the thiosulfate group, which has an oxidation potential of about 1 V (vs. SCE), numerous electron-accepting photosensitizer components that meet the requirement of Equation 3, can be used. Some compounds that meet the requirement of Equation 3 are listed below in TABLE I.

In general, sum of the electron-accepting photosensitizer component reduction potential and excitation energy is equal to or greater than the oxidation potential of the thiosulfate groups in the thiosulfate polymer. For example, this sum of reduction potential and excitation energy can be at least −1 V and up to and including +5 V (vs SCE), or more likely of at least −0.1 V and up to and including +3 V (vs SCE). Reduction potential and excitation energy can be determined for a given compound from sources in the literature or by measuring these parameters using cyclic voltammetry and UV-Vis spectrophotometery, respectively.

In general, derivatives from many different compounds can be used as electron-accepting photosensitizer components for thiosulfate group reactants, provided that the energetic requirements discussed above (in Equation 3) are satisfied. For example, the electron-accepting photosensitizer component can be an organic photosensitizer N-containing heterocyclic compound such as azinium salts, oxyazinium salts, thiazolium salts, pyrylium salts, naphthalene diimides, and naphthalene imides.

Representative electron-accepting photosensitizer components include but are not limited to, cyano-substituted carbocyclic aromatic compounds or cyanoaromatic compounds (such as 1-cyanonaphthalene, 1,4-dicyanonaphthalene, 9,10-dicyanoanthracene, 2-t-butyl-9,10-dicyanoanthracene, 2,6-di-t-butyl-9,10-dicyanoanthracene, 2,9,10-tricyanoanthracene, 2,6,9,10-tetracyanoanthracene), aromatic anhydrides and aromatic imides (such as 1,8-naphthylene dicarboxylic, 1,4,6,8-naphthalene tetracarboxylic, 3,4-perylene dicarboxylic, and 3,4,9,10-perylene tetracarboxylic anhydride or imide), condensed pyridinium salts (such as quinolinium, isoquinolinium, phenanthridinium, acridinium salts), and pyrylium salts. Useful electron-accepting photosensitizer components that involve the triplet excited state include but are not limited to, carbonyl compounds such as quinones (for example, benzo-, naphtho-, and anthro-quinones with electron withdrawing substituents such as chloro and cyano). Ketocoumarins especially those with strong electron withdrawing moieties such as pyridinium can also be used as electron-accepting photosensitizer components. These compounds can optionally contain substituents such as methyl, ethyl, tertiary butyl, phenyl, methoxy, and chloro groups that can be included to modify properties such as solubility, absorption spectrum, and reduction potential. The electron-accepting photosensitizer components used in the present invention can also be derived from the noted compounds.

These electron-accepting photosensitizer components can be used as individual materials in the compositions of this invention, or they can be used as precursors from which electron-accepting photosensitizer components are derived for covalent attachment to the thiosulfate polymers useful in the present invention, for example in recurring units derived from ethylenically unsaturated polymerizable monomers as described above. Attachment of the electron-accepting photosensitizer component to the thiosulfate polymer can improve the efficiency of the methods of this invention used for photo-patterning by allowing the thiosulfate components and the electron-accepting photosensitizer component in close proximity. In addition, attaching the electron-accepting photosensitizer components to the thiosulfate polymer can also reduce insolubility of the unattached corresponding components. PS-22 to PS-24 compounds listed below in TABLE I are examples of electron-accepting photosensitizer components comprising ethylenically unsaturated polymerizable vinyl groups, which components can be incorporated into thiosulfate polymers as described above.

Other useful electron-accepting photosensitizer components are inorganic salts or complexes such as transition metal salts and complexes, wherein the metal salts include but are not limited to, copper sulfate, nickel chloride, copper nitrate, zinc acetate, ferric chloride, and others that would be readily apparent to one skilled in the art using the teaching herein.

For example, the composition of this invention can further comprise a complexing metal ions, such as stannous, ferric, cobalt, silver, palladium, platinum, or gold ions.

Representative non-polymeric electron-accepting photosensitizer components PS-1 to PS-28 are shown in the following TABLE I:

TABLE I

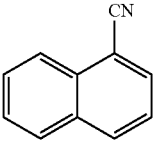 [SMILES: N#Cc1cccc2ccccc12] PS-1

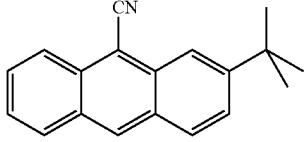 [SMILES: CC(C)(C)c1ccc2cc3ccccc3c(C#N)c2c1] PS-2

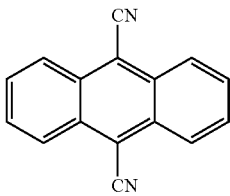 [SMILES: N#Cc1c2ccccc2c(C#N)c2ccccc12] PS-3

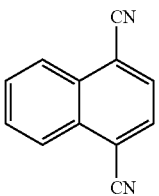 [SMILES: N#Cc1ccc(C#N)c2ccccc12] PS-4

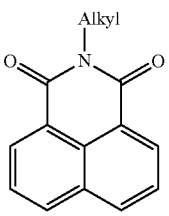 PS-5

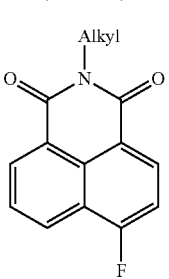 PS-6

TABLE I-continued

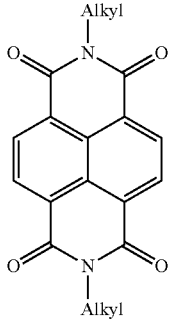 PS-7

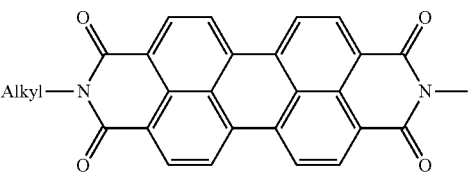 PS-8

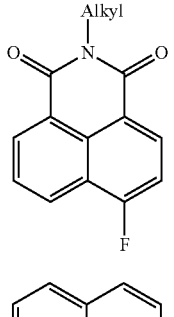 PS-9

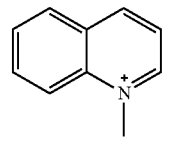 PS-10

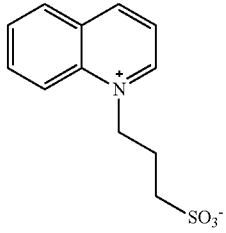 PS-11

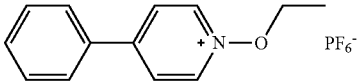 PS-12

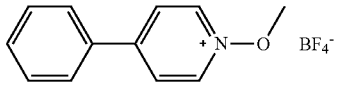 PS-13

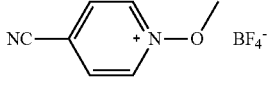 PS-14

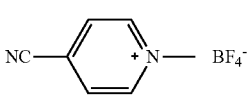 PS-15

TABLE I-continued
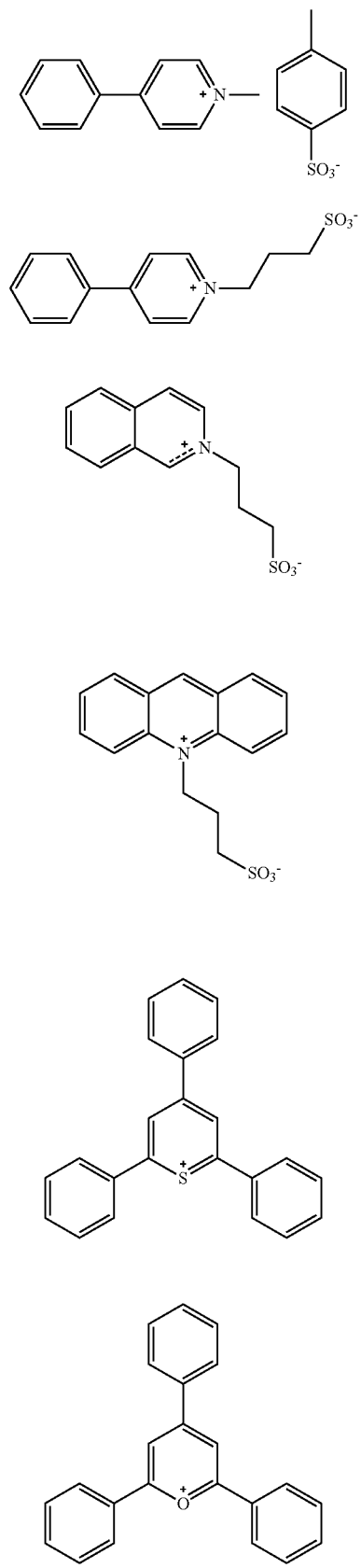
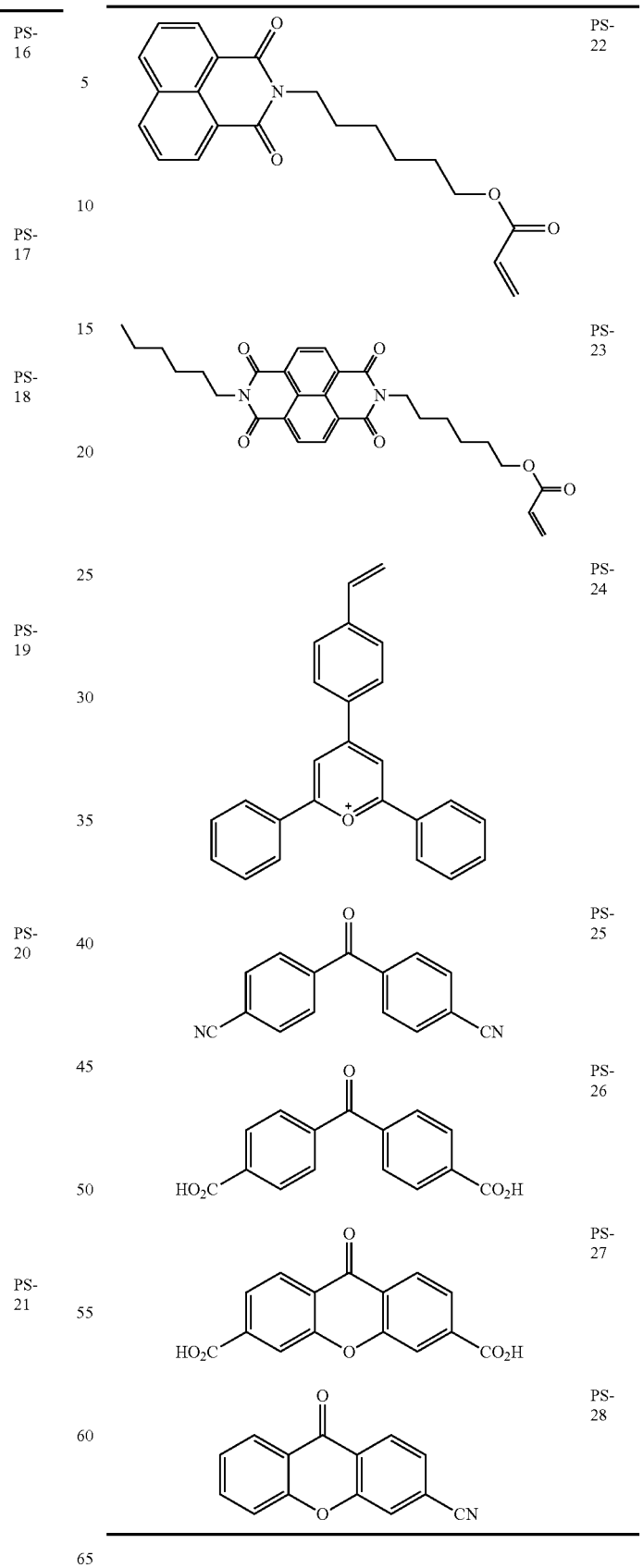
The composition of the invention can also contain optional ingredients such as a plasticizer, preservative, or surfactant, in individual or cumulative amounts of up to and including 15 weight %, based on total composition weight.

There are various ways to obtain compositions of the present invention. The following ways are representative but not meant to be limiting.

1) A non-crosslinked thiosulfate polymer can be thoroughly mixed with an appropriate electron-accepting photosensitizer component as a separate compound in an appropriate solvent of mixture of solvents.

2) A thiosulfate polymer can be thoroughly mixed with at least 0.1 weight % and up to and including 15 weight % of an appropriate electron-accepting photosensitizer component and an equimolar amount of a tetraalkyl ammonium halide salt in an appropriate solvent or mixture of solvents. Organic solvents that are soluble in water are useful in this mixture, including but not limited to tetrahydrofuran, acetone, ethyl methyl ketone, N-methyl pyrrolidone, dimethyl acetamide, and cyclopentanone. The exact amount of electron-accepting photosensitizer component depends upon its extinction coefficient and the eventual use.

3) An ethylenically unsaturated ethylenically polymerizable monomer comprising an electron-accepting photosensitizer component can be co-polymerized one or more monomers at least one of which includes the required thiosulfate.

4) An ethylenically unsaturated ethylenically polymerizable monomer comprising an electron-accepting photosensitizer component bearing covalently attached thiosulfate group can be co-polymerized with one or more ethylenically unsaturated polymerizable monomers.

5) A thiosulfate polymer in solution can be mixed with a metal salt to create a charge transfer complex.

A useful amount of resulting electron-accepting photosensitizer component in the resulting thiosulfate polymer can be at least 0.1 mol % and up to and including 10 mol % in relation to the molar amount of thiosulfate groups present in the thiosulfate polymer, composition, or polymeric layer. The exact amount of electron-accepting photosensitizer component can depends upon its extinction coefficient and application. This thiosulfate polymer can also comprise recurring units derived from other ethylenically unsaturated polymerizable monomers having different groups.

In some embodiments, the thiosulfate polymer composition of this invention can further comprise tetraalkyl ammonium ions including the same or different alkyl groups having 1 to 10 carbon atoms.

In such embodiments, the thiosulfate polymer can be a copolymer comprising, in random order: (a) recurring units comprising thiosulfate groups, (b) recurring units comprising the electron-accepting photosensitizer component, and additional (c) recurring units comprising pendant charged groups.

Articles

The thiosulfate polymer composition of any embodiment of the present invention can be in the form of a self-supporting slab or disk. It can also be a solution that is applied to or disposed onto a suitable support or substrate including but not limited to, polymeric films, glass, metals, stiff papers, or a lamination of any of these materials, and the support or substrate can be formed in any suitable shape. Polymeric film supports can be materials such as poly (ethylene terephthalate), poly(ethylene naphthalate), polycarbonate, polystyrene, cellulose acetate, inorganic polymeric materials such as certain glasses. In some embodiments, the support comprises a polyester or glass.

Thus, articles of the present invention can comprise a substrate having disposed thereon a coating comprising any of the thiosulfate polymer compositions of this invention, either in a continuous arrangement or in a predetermined pattern.

The support can also be a cylindrical surface and the thiosulfate polymer composition of this invention can be applied to its outer surface. The use of such cylinders is described for example in U.S. Pat. No. 5,713,287 (Gelbart), the disclosure of which is incorporated herein by reference.

The surface of the support or substrate can be treated in order to improve the adhesion of the thiosulfate polymer composition thereto. For example, the surface can be treated by corona discharge prior to applying the thiosulfate polymer composition of the present invention. Alternatively, an under-coating or subbing layer, such as a layer formed from a halogenated phenol or a partially hydrolyzed vinyl chloride-vinyl acetate copolymer, can be applied to the surface of the support prior to application of the thiosulfate polymer composition of this invention.

The thiosulfate polymer composition of this invention can be applied to the support and dried sufficiently to provide a dry thickness of at least 1 nm and up to and including 1 cm, or of at least 25 nm and up to and including 2000 nm. The applied layer can be uniformly over the entire substrate surface in a continuous or discontinuous manner, and it can be disposed in a random or predetermined pattern.

Methods of the Invention

During use of the thiosulfate polymer composition of the present invention, it is exposed to suitable radiation (such as UV or visible light) in a predetermined imagewise fashion, and the thiosulfate polymer composition can be exposed through a mask if desired, and the resulting exposed or non-exposed regions can be treated in a suitable manner to provide either a negative-working or positive-working pattern. When using a laser to expose (or image) the thiosulfate polymer composition of this invention, a diode laser is particularly useful because of its reliability and low maintenance, but other lasers such as gas or solid state lasers can also be used. The combination of power, intensity, and exposure time for laser imaging would be readily apparent to one skilled in the art.

As noted above, the thiosulfate groups in the thiosulfate polymer are capable of undergoing a chemical transformation from photochemical one electron oxidation, thus causing a change in solubility in the exposed regions of the exposed composition that can be provided on a suitable substrate. The photo-induced electron transfer reaction forms a product species, a process that defines the cross-linking event. New chemical bonds are formed between individual reactant moieties that results in a desired change in solubility in the exposed regions.

Scheme I below illustrates the photoinduced electron transfer induced reaction of the thiosulfate groups in the thiosulfate polymer. After the electron-accepting photosensitizer component (PS) has absorbed radiation, it oxidizes the thiosulfate ion to form a thiosulfuryl radical and an electron-accepting photosensitizer component radical anion (PS$^-$). In a subsequent step, the thiosulfuryl radical (—S—SO$_3$) fragments to generate a sulfur centered radical (—S) that dimerizes with another nearby sulfur radical to form a disulfide (—S—S—) bond (Scheme I). When the thiosulfate groups are in the polymer matrix, it is believed that the formation of the disulfide (S—S—) bonds provide the change in polymer solubility.

Scheme I

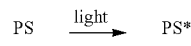

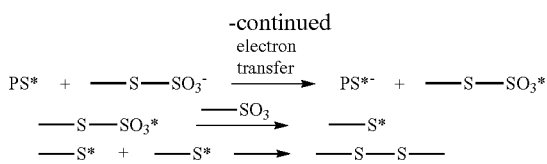

With the product formation, besides the change in solubility, changes in surface energy, glass transition temperature, and other optical properties such as refractive index and fluorescence properties, can also occur.

The thiosulfate polymer composition of this invention can be applied to a suitable substrate using any suitable means such as spray coating, roller or hopper coating, blade coating, spin coating, gravure coating, flexographic printing, or continuous or drop on demand ink jet printing. lithe thiosulfate polymer composition comprises a solvent, it can be evaporated or otherwise removed for example at least 50° C. and up to and including 70° C. using a suitable means such a heater or dryer. The conditions for thiosulfate polymer composition application and solvent removal would be readily apparent to a skilled artisan in manufacturing with suitable knowledge of the substrate and solvent properties. During drying, the temperature should remain below 120° C. to prevent thermal decomposition of the thiosulfate groups in the thiosulfate polymer.

During the methods of use, the thiosulfate polymer compositions and articles of the present invention can be exposed to suitable radiation, for example having a wavelength of at least 200 nm and up to but less than 725 nm, depending upon the spectral absorption of the electron-accepting photosensitizer component used in those embodiments.

A polymeric layer of the non-crosslinked thiosulfate polymer can be provided and irradiated with the noted radiation to photochemically react the thiosulfate polymer to provide a crosslinked polymer having disulfide groups in a predetermined pattern in the polymeric layer. The predetermined pattern can be provided using a mask layer, "digital irradiation" (as used in digital printing), or flexographic printing. Irradiation can be focused in the foreground or background areas of the thiosulfate polymer layer, depending upon whether the thiosulfate polymer layer is intended to function as a negative-working or positive-working system. When a laser is used to irradiate the thiosulfate polymer layer, it is can be a diode laser providing a radiation of a desired wavelength, because of the reliability and low maintenance of diode laser systems, but gas or solid state lasers can also be used. The combination of power, intensity and exposure time for laser imaging would be readily apparent to one skilled in the art. Irradiation efficiency can be improved when the thiosulfate polymer layer is thicker or also comprises one or more electron-accepting photosensitizer components (as defined above), either as separate compounds or as part of the thiosulfate polymer.

As noted above, the reactant thiosulfate group in the thiosulfate polymer is capable of undergoing a chemical transformation upon exposure and one electron oxidation, thus causing the change in solubility in the exposed regions of the thiosulfate polymer layer. The exposed areas of the thiosulfate polymer are crosslinked through generated disulfide bonds while the areas outside of the predetermined pattern remain non-crosslinked. The thiosulfate groups undergo a photo-induced electron transfer reaction to ultimately form a product species, a process that defines the cross-linking event. With the product formation, there are accompanying changes in solubility, surface energy, glass transition temperature, and other optical properties such as refractive index, fluorescence properties, or absorption spectrum. New chemical bonds, for example disulfide bonds, are formed between individual reactant moieties that results in a change in solubility.

Irradiation energy can be varied depending upon the thickness of the thiosulfate polymer layer, the concentration of thiosulfate groups in the irradiated thiosulfate polymer(s), the concentration of an electron-accepting photosensitizer component, the energy level of the irradiation, and other factors that would be readily apparent to one skilled in the art. For example, useful laser irradiation with a wavelength of at least 200 nm and up to and including 1200 nm can be carried out using energy of at least 0.01 $mJ/cm^2$.

After the irradiation and formation of crosslinked polymer, the thiosulfate polymer layer can be washed with a suitable solvent (such as an aqueous solution) to remove the non-crosslinked thiosulfate polymer while leaving the crosslinked polymer in the predetermined pattern. Water is a convenient solvent for removing (developing) the non-crosslinked thiosulfate polymer but other aqueous solutions are also useful, and they can be used at temperature or heated up to and below the boiling point of the aqueous solvent.

The remaining crosslinked thiosulfate polymer (with disulfide bonds) can then be treated with a suitable disulfide-reactive material. The most important reaction of disulfide bonds is their cleavage, for example using a reduction reaction. A variety of reductants can be used. In biochemistry, thiols such as mercaptoethanol (ME) or dithiothreitol (DTT) can be used as reductants. In organic synthesis, hydride agents are typically employed for scission of disulfides, such as borohydride. Alkali metals and certain transition metals such as gold, silver, and copper also cleave disulfide bonds. Such reactions can be used to selectively deposit silver, gold, or copper metals onto crosslinked polymers (having disulfide bonds) to make conductive patterns.

For example, the crosslinked thiosulfate polymer (with disulfide bonds) can be treated with a metal or metal salt that is reactive with the disulfide bonds. Examples of such metals and metal salts include but are not limited to, silver, gold, copper, nickel and iron, or salts thereof. Mixtures of metals or metal salts could be used. The treated crosslinked thiosulfate polymer can then be used to pattern conductive coatings, pattern surface energy modulation, and pattern bioreactivity.

Alternatively, a thiosulfate polymer composition of this invention can be used in a method comprising:
  providing a polymeric layer comprising a non-crosslinked thiosulfate polymer that also comprises pendant organic charged groups,
  photochemically reacting the non-crosslinked thiosulfate polymer to provide polymer layer areas comprising a crosslinked polymer having disulfide groups in the polymeric layer,
  optionally washing the polymeric layer to remove any non-crosslinked thiosulfate polymer while leaving the crosslinked polymer in the polymeric layer, and
  contacting the polymeric layer with a dispersion of metal nanoparticles to complex the metal nanoparticles with the crosslinked polymer having disulfide groups.

For example, this method can comprise contacting the polymeric layer with a dispersion of gold, silver, platinum, palladium, or copper nanoparticles.

In addition, the method can comprise photochemically reacting the non-crosslinked thiosulfate polymer to provide polymer layer areas in a predetermined pattern that comprise a crosslinked polymer having disulfide groups.

In such methods, the polymeric layer can comprise an electron-accepting photosensitizer component. Washing the polymeric layer to remove the non-crosslinked thiosulfate polymer can be carried out using an aqueous solution such as water.

In some embodiments, metal can be sequestered in the thiosulfate polymer composition after the polymeric layer is washed to remove non-crosslinked thiosulfate polymer. The remaining crosslinked thiosulfate polymer in the thiosulfate polymer layer can be treated with a metal ion solution to incorporate ions of the metal in the thiosulfate polymer layer areas comprising the crosslinked polymer. Metal ions useful for this purpose include but are not limited to, gold, silver, nickel, and copper ions, and can be supplied in a suitable aqueous solution (also include metal ion dispersions). The incorporated metal ions are reacted (reduced) to form nanoparticles of metal, and the metal nanoparticles can be electroless plated to obtain a coating of the metal in the predetermined pattern.

Yet another method relates to the hairdressing industry in which shaped hair (for example, human hair that has been shaped by a hairdresser) is treated or contacted with the thiosulfate polymer composition of the present invention comprising a thiosulfate polymer and an electron-accepting photosensitizer component having spectral absorption of up to and including 1200 nm. The thiosulfate polymer composition used in this method is typically in an aqueous solvent so it can be readily applied to shaped hair for a suitable period of time and washed or rinsed out when the treatment is completed. The thiosulfate polymer composition can be applied to all or only portions of the customer's shaped hair. This treatment of hair is sometimes known in the art as "setting" or "fixing" hair.

Once the thiosulfate polymer composition has been applied to the shaped hair, the contacted shaped hair (portion of shaped hair to which the composition has been applied) can be exposed to suitable radiation to provide disulfide groups in the thiosulfate polymer that are reactive with protein in the contacted shaped hair. Such radiation is typically available from fluorescent or incandescent light sources.

In general, a skilled hairdresser would know how to choose suitable time and temperature conditions to achieve the desired properties in the shaped hair of a customer. The shaped and treated hair can then be dried as is common in this industry.

Thus, in some other embodiments, the thiosulfate polymer composition of this invention can be used to shape hair in a hair treatment. Thus, a method for shaping hair, comprises:

transforming hair into shaped hair,
contacting the shaped hair with a composition comprising
a thiosulfate polymer comprising an electron-accepting photosensitizer component having spectral absorption of up to and including 1200 nm, as described herein, and
exposing the contacted shaped hair with radiation to provide disulfide groups in the thiosulfate polymer that are reactive with protein in the contacted shaped hair.

For example, contacting the shaped hair can be carried out for at least 0.5 minute and up to and including 20 minutes at a temperature of at least 20° C. Other details for shaping hair with the thiosulfate polymer composition of this invention would be readily apparent to one skilled in the art as described in various publications directed to shaping hair, such as in U.S. Pat. No. 5,071,641 (noted above) and U.S. Pat. No. 5,424,062 (noted above) the disclosures of which are incorporated herein.

The non-crosslinked thiosulfate polymer can be washed out of the shaped hair at a later time using any aqueous solution including a shampoo or conditioner.

For treating shaped hair, the thiosulfate polymer composition of this invention can additionally contain any or all of the following components commonly used in the hairdressing industry such as various protein dispersions, emulsifying agents, swelling agents (such as propylene glycol monomethyl ether), pH adjusting compounds, buffers, cosmetic agents (such as perfumes) lanolin derivatives, and thickening agents. For example, U.S. Pat. No. 5,242,062 (noted above) describes various additives useful in hair treating compositions in Columns 4 and 5, which disclosure is incorporated herein by reference.

The thiosulfate polymer composition of the present invention that is useful for treating shaped hair can be provided in diluted or concentrated solutions or dispersions (emulsions), as well as creams, gels, or pastes. The compositions can be delivered from bottles, pressurized aerosol cans, or any other suitable container.

Methods for Applying and Imaging Thiosulfate Polymer Compositions

The methods of the present invention can be carried out in several ways to provide articles of the present invention. For example:

1) A thiosulfate polymer composition can be applied to a suitable substrate;

2) The thiosulfate polymer composition coating can be then dried at from at least 40° C. and up to and including 50° C. for at least 1 minutes and up to and including 60 minutes;

3) The dried coating can be then exposed to radiation at an appropriate wavelength through a mask for an appropriate length of time (time of exposure is determined by the extinction coefficient of the electron-accepting photosensitizer component being used and thickness of the coating); and 4) The thiosulfate polymer composition in the unexposed areas of the coating can be washed away, if desired, using an aqueous solution such as plain water, and the thiosulfate polymer composition that is removed can be reused.

In some embodiments, metals can be deposited onto an imaged thiosulfate polymer composition coating as the metal will deposit only in imaged areas. There are multiple ways to achieve selective area deposition of a metal.

One method can comprise:

Applying a thiosulfate polymer composition of this invention to a suitable substrate;

Drying the coating at from 40° C. and up to and including 50° C. for at least 1 and up to and including 60 minutes;

Exposing the dried thiosulfate polymer composition coating to radiation of an appropriate wavelength through a suitable mask for an appropriate length of time (time of exposure is determined by extinction coefficient of the electron-accepting photosensitizer component being used and thickness of the coating);

Optionally washing the dried and exposed thiosulfate polymer composition coating with water or another aqueous solution to wash away thiosulfate polymer composition in unexposed (non-imaged) areas to obtain an image on the substrate; and the thiosulfate polymer composition that is washed away can be reused;

Applying a conductive metal precursor salt solution to the exposed (imaged) areas on the substrate;

Adding a reducing agent to the substrate;

Optionally washing the exposed (imaged) areas on the substrate with water or another aqueous solution; and Depositing a suitable metal (for example as a dispersion) on exposed (imaged) areas on the substrate.

Another method of this invention comprises:

Coating a thiosulfate polymer composition onto a substrate;

Drying the thiosulfate polymer composition coating at from 40° C. and up to and including 50° C. for at least 1 and up to and including 60 minutes;

Exposing the dried coating to radiation of an appropriate wavelength through a mask for an appropriate length of time (time of exposure is determined by extinction coefficient of the electron-accepting photosensitizer component being used and thickness of the dried coating);

Washing the dried coating with water or another aqueous solution to wash away thiosulfate polymer composition in the unexposed (non-imaged) areas to obtain an image on the substrate, and the thiosulfate polymer composition that is washed away from the unexposed (non-imaged) areas can be reused;

Dipping the imaged substrate into or applying a metal nanoparticle containing solution; and Optionally washing the substrate with an aqueous solution so that metal nanoparticles are deposited only on the imaged (exposed) areas on the substrate.

In yet another embodiment, the method of this invention can include:

Coating a thiosulfate polymer composition of this invention onto a substrate;

Drying the thiosulfate polymer composition coating at from 40° C. and up to and including 50° C. for at least 1 and up to and including 60 minutes;

Exposing the dried thiosulfate polymer composition to radiation of appropriate wavelength through a mask for appropriate length of time (the time of exposure is determined by the extinction coefficient of the electron-accepting photosensitizer component being used and thickness of the coating);

Washing the dried thiosulfate polymer composition with water or another aqueous solution to wash away thiosulfate polymer composition in the unexposed (non-imaged) areas to obtain an image on the substrate, and the thiosulfate polymer composition that is washed away from the unexposed (non-imaged) areas can be reused.

Dipping or contacting the imaged substrate with a conductive metal precursor salt solution for an appropriate length of time; and Washing the imaged substrate with a solution of a reducing agent so that metal nanoparticles are formed only in the imaged areas on the substrate.

Also provided is a method for electroless plating using the thiosulfate polymer composition. Currently, electroless metal plating treatment can be used to form a conductive coating film on an insulating object (for example, an insulative layer). The electroless metal plating treatment can be carried out through a procedure having the following steps.

A conditioning step can be carried out using various surfactants to clean a substrate surface and to enable the surface to carry charges. A catalyst-coating step can be carried out using a tin/palladium colloid bath. An activation step can be then carried out using hydrofluoric acid or another strong acid to activate the catalyst colloid that is adsorbed on the substrate surface. Electroless metal plating can then be carried out using a plating bath containing a reducing agent such as formalin. When the substrate for the electroless metal plating treatment is a printed circuit board for example, carrying a pattern, the pattern can be formed with various methods, such as, but not limited to, the subtractive method, semi-additive method, and full-additive method.

Other methods, such as primer treatment using palladium or silver catalyst can also be used. In the primer treatment, a metal catalyst is introduced into a resin material containing solvent and inorganic filler. The resin material is coated onto a substrate to form a resin film containing a catalyst. Then, electroless metal plating is carried out to form a conductive film. The primer treatment is mainly used on a plastic surface for the purpose of electromagnetic interference (EMI) shielding.

In the semiconductor field, sputtering and chemical vapor deposition (CVD) are more commonly used for the formation of a conductive layer and the manufacturing technology has been established.

Moreover, a technology of introducing an organic metal salt with catalytic activity into a resin material and then forming a conducting film with the resin material is disclosed in U.S. Pat. No. 5,059,242 (Firmstone et al.) and has been used in the process of electrode formation.

In electroless metal plating processes, the insulating resin material in the printed circuit board and semiconductor device is first treated with dry etching or by using an agent such as permanganic acid to generate a rough surface and to improve wettability. Then, electroless copper plating or electroless nickel plating can be conducted to form a conducting layer on the surface of the resin material.

However, it is very difficult to introduce a carboxyl group or a hydroxyl group into the resin matrix of a highly reliable insulating resin material. The carboxyl group or hydroxyl group may reduce the reliability of the insulating resin material. As a result, the conducting layer formed through electroless metal plating has low adhesive strength to the surface of the insulating resin material. Moreover, for the materials not suitable for generating these anchoring groups, such as glass or ceramics to improve the attachment of a metal conductive layer, the metal conductive layer formed through electroless metal plating will also have low adhesive strength to the surface.

In the process of forming a conductive layer on a base material, currently the surface of the base material is first treated with oxygen plasma and then the conductive layer is formed with sputtering. Moreover, a conductive layer with the required thickness can be formed by this method by further electrolytic metal plating. However, although sputtering is a standard method for the formation of a thin layer, the process of sputtering usually takes a long period of time and the metal target is expensive. Therefore, the cost of the sputtering process is relatively high.

On the other hand, the method for the formation of a conductive layer with an organic metal salt uses a resinate compound of palladium, silver, or platinum. Such compound can be dissolved in water or an organic solvent and the substrate to be coated is dipped into the solution to form a coating layer of the resinate compound. Then, thermal decomposition of the resinate compound generates a metal thin layer on the substrate to be coated. Finally, electroless or electrolytic metal plating can be carried out to form a conductive layer. By using this method, however, the metal coating layer obtained has poor uniformity. In fact, the metal powder is simply attached to the surface of the substrate to be coated and the attachment is not very strong. In order to solve the problem, a paste is prepared by introducing. the metal resinate into a synthetic resin material, which is then coated on the substrate to form a uniform coating layer. The paste is widely used to fill holes on printed circuit boards and form electrodes on LCD through screen printing.

However, the conducting paste is not suitable for semiconductors and semiconductor packages as well as other purposes requiring a high reliability. Moreover, it is very difficult to form fine lines through screen printing of the paste. In other words, when using an organic metal salt in the formation of electronic devices, a paste can be first prepared by introducing an organic metal salt to a synthetic resin material and coating it onto a substrate through screen printing, followed by sintering to convert the organic metal salt to the corresponding metal. In this process, the sintering temperature must be higher than the thermal decomposition temperature of the organic metal salt (at least 300° C.) to remove the synthetic resin material. Therefore, when the synthetic resin material is completely removed, only the metal pattern remains. However, when the method is used in the formation of semiconductor packages, since the base body of semiconductor packages is made of a composite material of epoxy resin reinforced with glass fiber, the high temperature used in the sintering step will cause thermal damage, such as deformation or cracks, on the base body. In addition, since the synthetic resin material is completely removed in the sintering step, various defects, such as pinholes or wire breakage can be generated in the metal pattern obtained after sintering. In order to avoid these problems, a paste with a high metal content can be used. More specifically, when using a paste containing a gold resinate to form a gold wire, the gold content in the paste must be as high as 25 weight % and the sintering temperature about 500° C. In other words, the sintering step in the coating method will cause severe damage to the substrate to be coated. In order to form a metal pattern with a high reliability, the content of the expensive metal in the paste should be increased significantly, resulting in high production costs.

A purpose of this invention is to solve the problems mentioned above and to provide a thiosulfate polymer composition after imaging step that forms an organic functionality where metal nanoparticles can be selectively absorbed. In a separate step, these metal centers can act as seed sites for electroless metal plating.

The electroless metal plating method can include any commonly used electroless metal plating for depositing a metal selected from copper, nickel, gold, tin, zinc, silver, and cobalt as well as an alloy of these metals. There is no special limitation on the metal, plating bath, and plating conditions used in the electroless metal plating treatment.

The metal element used can be determined based on the electroless metal plating treatment. Any metal element can be used for the purpose as long as the metal element is able to provide a catalytic activity of metal deposition suitable for electroless metal plating. Examples of the catalytic metal element include but are not limited to, palladium, silver, platinum, rhodium, indium, and ruthenium. In consideration of production cost and plating efficiency, tin or silver is particularly useful as the catalytic metal element for electroless metal plating of a copper, nickel, or nickel alloy.

For example, a method can comprise:

Providing a photolithographic pattern-forming thiosulfate polymer composition of this invention as a coating in a multilayered integral body that comprises: (a) a substrate; (b) a photosensitive layer formed on one surface of the substrate (a), the photosensitive layer formed from the thiosulfate polymer composition;

Exposing the coating provided above to actinic radiation;

Optionally washing away the coatings from the first two steps using an aqueous solution (such as water); and Dipping the coating remaining from the prior step in a nanoparticle solution.

The present invention provides at least the following embodiments and combinations thereof, but other combinations of features are considered to be within the present invention as a skilled artisan would appreciate from the teaching of this disclosure:

1. A composition comprising a thiosulfate polymer and an electron-accepting photosensitizer component, provided that when the electron-accepting photosensitizer component is not covalently attached to the thiosulfate polymer, it has a spectral absorption of less than 750 nm.

2. The composition of embodiment 1, wherein the electron-accepting photosensitizer component is a metal complex electron-accepting photosensitizer component.

3. The composition of embodiment 2, which has a spectral absorption that is different from the spectral absorption of either the thiosulfate polymer or the metal complex electron-accepting photosensitizing component alone.

4. The composition of any of embodiments 1 to 3, wherein the sum of the electron-accepting photosensitizer component reduction potential and excitation energy is equal to or greater than the oxidation potential of the thiosulfate group in the thiosulfate polymer.

5. The composition of any of embodiments 1 to 4, wherein the electron-accepting photosensitizer component is a covalently-connected component of the thiosulfate polymer.

6. The composition of embodiment 5, wherein the thiosulfate polymer is a copolymer comprising, in random order: (a) recurring units comprising thiosulfate groups, and (b) recurring units comprising the electron-accepting photosensitizer component.

7. The composition of embodiment 6, wherein the copolymer further comprises, in random order, (c) recurring units other than the (a) and (b) recurring units, which (c) recurring units comprise a pendant charged group, and the (c) recurring units are present in an amount of at least 0.1 mol %, based on the total recurring units in the copolymer.

8. The composition of embodiment 7, wherein the additional (c) recurring units comprise a pendant carboxy, carboxylate, phospho, phosphonate, phosphate, sulfo, sulfonate, or sulfite group.

9. The composition of claim 7 or 8, wherein the (c) recurring units are present in an amount of at least 0.1 mol % up to and including 50 mol %.

10. The composition of any of claims 7 to 9, wherein the (c) recurring units are present in the copolymer in an amount of up to 50 mol %, the (a) recurring units are present in the copolymer in an amount of at least 1 mol %, and the copolymer further comprises (d) recurring units that have a total neutral charge and are present in an amount of at least 1 mol % and up to and including 49 mol %.

11. The composition of claim 10, wherein the molar ratio of the (a) recurring units to the (d) recurring units is from 1:3 to 3:1.

12. The composition of any of claims 1 to 5, comprising (a) recurring units comprising thiosulfate groups, and (c) recurring units that comprise a pendant charged group in an amount of at least 0.1 mol %.

13. The composition of any of embodiments 1 to 12, wherein the electron-accepting photosensitizer component is present in an amount of at least 0.1 mol % and up to and including 10 mol %, in relation to the molar amount of thiosulfate groups present in the composition.

14. The composition of any of embodiments 1 to 4, 12 and 13, wherein the electron-accepting photosensitizer component is a compound separate from the thiosulfate polymer.

15. The composition of any of embodiments 1 to 14, wherein the electron-accepting photosensitizer component is an organic photosensitizer N-containing heterocyclic compound.

16. The composition of any of embodiments 1 to 15, wherein the electron-accepting photosensitizer component is an inorganic salt or complex.

17 The composition of any of embodiments 1 to 16, wherein the electron-accepting photosensitizer component is selected from the group of compounds consisting of cyanoaromatic compounds, aromatic anhydrides, aromatic imides, condensed pyridinium salts, pyrylium salts, and quinines, or the electron-accepting photosensitizer component is derived from one of these compounds.

18. The composition of any of embodiments 1 to 17 further comprises a complexing metal ion.

19. The composition of any of embodiments 1 to 18, further comprising tetraalkyl ammonium ions.

20. An article comprising a substrate having disposed thereon a coating comprising the composition of any of embodiments 1 to 19.

21. The article of embodiment 20, wherein the coating is disposed in a predetermined pattern.

The following Examples are provided to illustrate the practice of this invention and are not meant to be limiting in any manner.

Synthesis 1

Preparation of Poly(vinyl benzyl thiosulfate sodium salt-co-methyl methacrylate)

A representative thiosulfate polymer useful in the practice of the present invention was prepared as follows:

Vinyl benzyl chloride (10 g, 0.066 mol), methyl methacrylate (26.23 g, 0.262 mol), and AIBN (1.08 g, 7 mmol) were dissolved 180 ml of toluene. The resulting solution was purged with dry nitrogen and then heated at 65° C. overnight. After cooling the solution to room temperature, it was dropwise added to 2000 ml of methanol. The resulting white powdery copolymer was collected by filtration and dried under vacuum at 60° C. overnight. 1H NMR analysis indicated that the resulting copolymer contained 30 mol % of recurring units derived from vinyl benzyl chloride.

A sample of this copolymer (18 g) was dissolved in 110 ml of N,N-dimethyl formamide (DMF). To this solution was added sodium thiosulfate (9 g) and 20 ml of water. Some polymer precipitated out. The cloudy reaction mixture was heated at 70° C. for 24 hours. After cooling to room temperature, the hazy reaction mixture was transferred to a dialysis membrane and dialyzed against water. A small amount of the resulting polymer solution was freeze dried for elemental analysis and the rest was stored and used as a solution. Elemental analysis indicated that all the benzyl chloride groups in the copolymer were converted to sodium thiosulfate salt to provide a thiosulfate polymer useful in the present invention.

Synthesis 2

Preparation of N-Butyl-N'-[2-(ethoxy-2-acrylate) ethyl]-1,4,5,8-naphthalenetetraearboxylic diimide A representative ethylenically unsaturated monomer useful to provide thiosulfate polymers of the present invention was prepared as follows:

Step 1-Synthesis of the monopotassium salt (half anhydride), 1-potassium carboxylate-8-carboxylic acid naphthalene-4,5-dicarboxylic anhydride:

A 12-liter, four-neck round bottom flask fitted with a mechanical stirrer and a condenser was charged with potassium hydroxide (454 g, 7.60 mol) and water (6 liters), followed by the addition of 1,4,5,8-naphthalenetetra-carboxylic dianhydride (462 g, 1.72 mol). The reaction mixture was stirred for 1 hour and a clear solution resulted. Phosphoric acid, 85% (613 g 5.2 mol) in water (900 ml) was added over 45 minutes, the reaction solution was stirred overnight, and the resulting solid product was collected by filtration (yield close to 100%.) The spectral data were consistent with its assigned structure.

Step 2-Synthesis of monoimide, naphthalenetetracarboxylic-1,8-N-butylimide-4,5-anhydride:

A 12-liter, four-neck round bottom flask fitted with a mechanical stirrer and a condenser was charged with the monopotassium salt from Step 1 (169.2 g, 0.52 mol) and water (5 liters) to give a milky brown-colored suspension. Butyl amine (240 g, 3.12 mol) was added all at once and a clear amber-colored solution was formed. The reaction solution was heated to 90-95° C. for 1 hour. Concentrated hydrochloric acid (690 ml) dissolved in 700 ml of water was added dropwise to the hot reaction solution and heating was continued for 2 hours. During the addition, the temperature did not exceed 95° C. Heat was removed and the reaction was allowed to stir overnight at room temperature. The resulting precipitate was collected on a glass *frit* to give 150 g of the desired product at 90% yield. Spectral data were consistent with the assigned compound structure.

Step 3-Synthesis of diimide, N-butyl-N'-[2-(2-hydroxyethoxy)-ethyl]-1,4,5,8-naphthalenetetraccarboxylic diimide:

A 12-liter, four-neck round bottom flask fitted with a mechanical stirrer and a condenser was charged with naphthalene butylimide monoanhydride (434 g, 1.4 mol) from Step 2, 2-(2-aminoethoxyethanol (230 g, 2.2 mol), and N-methyl pyrrolidone (1.2 liters). The reaction solution was heated to 140-150° C. for 3 hours. The reaction solution was then allowed to cool for 30 minutes and the reaction flask was filled with methanol and a pink-colored solid precipitated. The reaction solution was stirred overnight and the resulting solid was collected on a glass frit to give 522 g of crude product (90% yield). Purification was carried out using dichloromethane on a silica gel column, providing 313 g of product (54% yield). The spectral data were consistent with the assigned compound structure.

Step 4-Coupling of naphthalene bisimide alcohol with acryloyl chloride, N-butyl-N'-[2-(ethoxy-2-acrylate)ethyl]-1,4,5,8-naphthalene-tetracarboxylic diimide with acyloyl chloride:

A 5-liter, four-neck round bottom flask fitted with a mechanical stirred, condenser and a nitrogen inlet was charged with the hydroxyl ether naphthalene butyl bisimide of Step 3 (246 g, 0.6 mol) and triethylamine (73 g, 0.72 mol, 100 ml) in dichloromethane (2 liters). Acryloyl chloride (63 g, 0.7 mol, 57 ml) in dichloromethane (DCM, 150 ml) was added dropwise, solubilizing the reactants and the reaction solution was stirred at room temperature overnight. The reaction solution was washed with 5% hydrochloride acid (200 ml), forming an emulsion. Methanol was added to break up the emulsion. The organic products were washed with water and dried over magnesium sulfate. The resulting product was purified on silica column using ligroin/DCM mixture at 1/1 then increasing to 100% DCM to elute the product. The spectral data were consistent with the assigned compound structure.

Synthesis 3

Preparation of 1,8-Naphthalimidohexyl Acrylate

A representative ethylenically unsaturated monomer useful to provide thiosulfate polymers of the present invention was prepared as follows:

Step 1-Synthesis of 1,8-Naphthalimidohexanol:

A 200 ml round bottom flask fitted with condenser, nitrogen inlet, and stirring magnet was charged with 1,8-naphthalic anhydride (10 g, 50.5 mmole), 6-amino-1-hexanol (6 g, 51.0 mmole), and 150 ml of N-methyl-2-pyrrolidone. The reaction mixture was warmed to 140° C. for 20 hours. The reaction mixture was then cooled and poured into excess ice water. A resulting brown precipitate was filtered and recrystalyzed from heptane to give 5 g of a tan colored solid (30% yield). The spectral data were consistent with assigned compound structure.

Step 2-Synthesis of 1,8-Naphthalimidohexyl acrylate:

A 200 ml 3-neck round flask with a nitrogen inlet, and stirring magnet was charged with the 1,8-naphthalimidohexanol (2.1 g, 7.1 mmole) and 60 ml of anhydrous dichloromethane.

Once dissolved, triethylamine (0.9 g, 9.2 mmole) was added. To this stirring mixture was slowly added acryloyl chloride (0.8 g, 9.2 mmole). The reaction mixture was allowed to stir at room temperature for 24 hours. The reaction mixture was washed once with 10% HCl, then with water and dried over magnesium sulfate, and the solvent was removed in vacuo to provide a yellow semisolid. The resulting crude product was purified by running it through column of silica with dichloromethane to elute the final product. The spectral data were consistent with the assigned compound structure.

Synthesis 4

Preparation of Poly(2-hydroxy-2-thiosulfate sodium salt propyl methacrylate-co-methyl methacrylate)

The procedure of Synthesis 1 was followed using glycidyl methacrylate (18.2 g, 0.128 mol), methyl methacrylate (30.0 g, 0.300 mol), 2,2'-azobis(2-methylbutyronitrile) (0.82 g, 0.004 mol), and 192 ml of toluene. The reaction temperature was 70° C. 1H NMR analysis indicated that the resulting precursor polymer contained 35 mol % of recurring units derived from glycidyl methacrylate Analysis by size exclusion chromatography (SEC) indicated a weight average molar mass of 45,800 (polystyrene standards)

The desired thiosulfate polymer was prepared as described for Synthesis 1 using 30.0 g of precursor polymer, 140 ml of DMF, 16.8 g of sodium thiosulfate, and 28 ml of water. The temperature of the reaction solution was 70° C. for 24 hours. The thiosulfate polymer glass transition temperature was determined to be 107.5° C. by Differential Scanning calorimetry (DSC).

Inventive Example 1

Preparation of Poly(vinyl benzyl thiosulfate sodium salt-co-methyl methacrylate-co-N-butyl-N'-[2-(ethoxy-2-acrylate)ethyl]-1,4,5,8-naphthalenetetracarboxylic diimide)

The procedure of Synthesis 1 was followed using vinyl benzyl chloride (4.2 g, 0.027 mol), methyl methacrylate (8.5 g, 0.085 mol), the noted diimide (1.1 g, 0.002 mol), 2,2'-azobis(2-methylbutyronitrile) (0.33 g, 0.002 mol), and 47 ml of toluene. The reaction temperature was 70° C. 1H NMR analysis indicated that the resulting precursor polymer contained 30 mol % of recurring units derived from vinyl benzyl chloride. Analysis by size exclusion chromatography (SEC) indicated a weight average molar mass of 17,800 (polystyrene standards).

The desired thiosulfate polymer was prepared as described in Synthesis 1 using 1.35 g of precursor polymer, 50 ml of DMF, 1.5 g of sodium thiosulfate, and 10 ml of water. The temperature of the reaction solution was 90° C. for 8 hours. The thiosulfate polymer glass transition temperature was determined to be 99.8° C. by Differential Scanning calorimetry (DSC).

Inventive Example 2

Preparation of Poly(vinyl benzyl thiosulfate sodium salt-co-methyl methacrylate-co-acrylic acid-co-N-butyl-N'-[2-(ethoxy-2-acrylate)ethyl]-1,4,5,8-naphthalene-tetracarboxylic diimide)

The procedure of Synthesis 1 was followed using vinyl benzyl chloride (8.2 g, 0.053 mol), methyl methacrylate (8.5 g, 0.085 mol), acrylic acid (8.5 g, 0.119 mol), the diimide (2.3 g, 0.005 mol), 2,2'-azobis(2-methylbutyronitrile) (0.76 g, 0.004 mol), and 90 ml of dioxane. The reaction temperature was 70° C. 1H NMR analysis indicated that the resulting precursor polymer contained 30 mol % of recurring units derived from vinyl benzyl chloride. Analysis by size exclusion chromatography (SEC) indicated a weight average molar mass of 41,600 (polystyrene standards).

The desired thiosulfate polymer was prepared as described in Synthesis 1 using 26.1 g of precursor polymer, 285 ml of DMF, 8.5 g sodium thiosulfate, and 57 ml of water. The temperature of reaction was held at 90° C. for 8 hours. The glass transition temperature of the resulting thiosulfate polymer was determined to be 195° C. by Differential Scanning calorimetry (DSC).

Inventive Example 3

Preparation of Poly(vinyl benzyl thiosulfate sodium salt-co-acrylic acid-co-N-butyl-N'-[2-(ethoxy-2-acrylate)ethyl]-1,4,5,8-naphthalenetetracarboxylic diimide)

The procedure of Synthesis 1 was followed using vinyl benzyl chloride (7.3 g, 0.048 mol), acrylic acid (15.0 g, 0.21 mol), the diimide (1.9 g, 0.005 mol), 2,2'-azobis(2-methylbutyronitrile) (0.76 g, 0.004 mol), and 73 ml of dioxane. The reaction temperature was 70° C. 1H NMR analysis indicated that the resulting precursor polymer contained 31 mol % of recurring units derived from vinyl benzyl chloride. Analysis by size exclusion chromatography (SEC) indicated a weight average molar mass of 21,400 (polystyrene standards).

The desired thiosulfate polymer was prepared as described in Synthesis 1 using 20.0 g of precursor polymer, 250 ml of DMF, 6.5 g sodium thiosulfate, and 50 ml of water. The reaction temperature was 90° C. for 8 hours to provide the desired thiosulfate polymer that had a glass transition temperature of 200° C. as determined by DSC.

Inventive Example 4

Preparation of Poly(vinyl benzyl thiosulfate sodium salt-co-methyl methacrylate-co-1,8-naphthalimidohexyl acrylate)

The procedure of Synthesis 3 was followed using vinyl benzyl chloride (3.5 g, 0.023 mol), methyl methacrylate (7.7 g, 0.077 mol), the imide (0.5 g, 0.001 mol), 2,2'-azobis(2-methylbutyronitrile) (0.29 g, 0.002 mol), and 40 ml of toluene. 1H NMR analysis indicated that the desired precursor polymer contained 34 mol % of recurring units derived from vinyl benzyl chloride, and analysis by size exclusion chromatography (SEC) indicated a weight average molar mass of 25,800 (polystyrene standards).

The desired thiosulfate polymer was prepared as described in Synthesis 1 using 8.0 g of precursor polymer, 40 ml of DMF, 3.9 g of sodium thiosulfate, and 8 ml of water. The reaction temperature was held at 90° C. for 8 hours to provide the desired thiosulfate polymer that had a glass transition temperature of 111° C. as measured by DSC.

Inventive Example 5

Preparation of Poly(vinyl benzyl thiosulfate sodium salt-co-methyl methacrylate-co-acrylic acid-co-1,8-naphthalimidohexyl acrylate)

The procedure of Synthesis 1 was followed using vinyl benzyl chloride (3.0 g, 0.02 mol), methyl methacrylate (3.6 g, 0.036 mol), acrylic acid (3.0 g, 0.04 mol), the imide (0.4 g, 0.001 mol), 2,2'-azobis(2-methylbutyronitrile) (0.28 g, 0.002 mol), and 30 ml of dioxane. 1H NMR analysis indicated that the resulting precursor polymer contained 33 mol % of vinyl benzyl chloride, and analysis by SEC indicated a weight average molar mass of 45,200 (polystyrene standards).

The desired thiosulfate polymer was prepared as described in Synthesis 3 using 4.2 g of the precursor polymer, 22.5 ml of DMF, 2.1 g of sodium thiosulfate, and 4.5 ml of water. The reaction temperature was held at 90° C. to provide the desired thiosulfate polymer that had a glass transition temperature of 119° C. as determined by DSC.

Inventive Example 6

Imaging Thiosulfate Polymer Composition Coating

To 1 ml of an 8 weight % solution of poly(vinyl benzyl thiosulfate sodium salt-co-methyl methacrylate) (prepared as described above in Synthesis 1) in water, was added a solution of 1.7 mg of 4-phenyl-N-ethoxy pyridinium hexafluorophosphate of electron-accepting photosensitizer component PS-12 in 1 ml of tetrahydrofuran (THF). The resulting thiosulfate polymer composition was stirred and then spin-coated on glass plate (as a substrate) at 1000 rpm. The thiosulfate polymer composition coating was protected from UV and blue light at all times. The thiosulfate polymer composition coating was dried for 5 minutes on a hot plate at 50° C. The dry thickness of the resulting layer was measured by spectral reflectance method using a Filmetrics single spot measurement unit and analyzed using a FilMeasure version 4.17.7 software program, and was found to be 0.8 μm. The coated thiosulfate polymer composition was exposed to light using the mercury lamp (EXFO Acticure® spot curing system) through a mask for 10 seconds and the coated thiosulfate polymer composition was then washed with water, followed by washing with acetone. The exposed regions of the coated composition on the glass plate were rendered insoluble, forming the mask image in the coated layer on the substrate, whereas the coated thiosulfate polymer composition in the non-exposed regions of the coated thiosulfate polymer composition was washed away.

This example demonstrates that the thiosulfate polymer composition of the present invention can be used to provide an article that can be appropriately imaged to provide a photoresist of the thiosulfate polymer composition on a substrate.

Inventive Example 7

Preparation of a Polyurethane Thiosulfate Polymer

Polycarbonate polyol $M_w$ 2000 (5.4 g, 0.004 mol), 2,3-dibromo-1,4-butanediol (1.9 g, 0.008 mol), and a catalytic amount of dibutyltin diluarate were dissolved in 12 ml of tetrahydrofuran. The resulting solution was heated at 65° C. under nitrogen. To this solution was added dropwise isophorone diisocyanate (2.5 g, 0.011 mol) dissolved in 2.5 ml of tetrahydrofuran. The solution was then warmed at 75° C. for 20 hours. After cooling, the solution was added dropwise to heptane. The resulting glassy polymer was collected and dried under vacuum at 60° C. overnight. 1H NMR analysis indicated that the resulting polymer contained 24 mol % of recurring units derived from 2,3-dibromo-1,4-butanediol. Analysis by size exclusion chromatography (SEC) indicated a weight average molar mass of 20,600 (polystyrene standards).

A sample of the resulting polymer (3.0 g) was dissolved in 25 ml of N,N-dimethyl formamide (DMF). To this solution was added sodium thiosulfate (1.5 g) dissolved in 5 ml of water. Some thiosulfate polymer precipitated out. The cloudy reaction mixture was then heated at 70° C. for 24 hours. After cooling to room temperature, the hazy reaction mixture was transferred to a dialysis membrane and dialyzed against water.

Comparative Example 1

Imaging Thiosulfate Polymer Coating

To 1 ml of an 8 weight % solution of poly(vinyl benzyl thiosulfate sodium salt-co-methyl methacrylate) (prepared as described in Synthesis 1) in water, was added 1 ml of tetrahydrofuran. The resulting thiosulfate polymer composition was stirred and then spin-coated onto a glass plate (as a substrate) at 1000 rpm. The thiosulfate polymer composition coating was protected from UV and blue light at all times. The thiosulfate polymer composition coating was then dried for 5 minutes on a hot plate at 50° C. The dry thickness of the coated layer was measured as described in Inventive Example 6, and found to be 0.8 μm. The coated layer was exposed to light using a mercury lamp (EXFO Acticure® spot curing system) through a mask for 10 seconds and then washed with water, followed by washing with acetone. All non-crosslinked thiosulfate polymer in the coated layer was washed away, and no image was detected on the substrate. This example demonstrates that using a thiosulfate polymer composition comprising only the thiosulfate polymer is ineffective to provide an imageable article.

Inventive Example 8

Photopatterning Thiosulfate Polymer Composition Coating

To 1 ml of an 11 weight % solution of poly(vinyl benzyl thiosulfate sodium salt-co-methyl methacrylate) (prepared in Synthesis 1) in water, 0.066 weight % of 4-phenyl-N-ethoxy pyridinium hexafluorophosphate of electron-accepting photosensitizer component PS-12, 1.1 weight % of tetrabutylammonium chloride, and 1 ml of tetrahydrofuran was added and then spin-coated onto a glass plate support at 1000 rpm. The resulting thiosulfate polymer coating was protected from UV and blue light at all times. The coating was then dried for 5 minutes on a hot plate at 50° C. The thiosulfate polymer coating was then exposed to light using a mercury lamp through a mask for 10 seconds and then washed with water, followed by washing with acetone. The exposed areas of the thiosulfate polymer coating on the glass plate were rendered insoluble (crosslinked), forming an image corresponding to the mask, whereas non-crosslinked thiosulfate polymer in the unexposed areas of the thiosulfate polymer coating was washed away.

The results show that a thiosulfate polymer composition of the present invention can be used to prepare a photoresist with an image.

Inventive Example 9

Demonstration of Photoinduced Electron Transfer

To 1 ml of a 2 weight % solution of poly(vinyl benzyl thiosulfate sodium salt-co-methyl methacrylate-co-acrylic acid-co-N-butyl-N'-[2-(ethoxy-2-acrylate)ethyl]-1,4,5,8-naphthalenetetracarboxylic diimide) (prepared in Inventive Example 5) in water, 1 ml of tetrahydrofuran was added and the solution was then spin-coated onto a glass plate support at 1000 rpm. The resulting thiosulfate polymer coating was protected from UV and blue light at all times, and dried for 5 minutes on a hot plate at 50° C. Absorption spectra of the thiosulfate polymer coating were recorded before and after exposure to light. After exposure to light, the characteristic absorption spectrum of naphthalenediimide radical anion (compared with a chemically generated authentic spectrum) was observed. Formation of naphthalene diimide radical anion was concomitant with photo-crosslinking as evidenced by a change in solubility of the thiosulfate polymer coating.

These results show that the thiosulfate polymer composition of the present invention was photocrosslinked by photoinduced electron transfer to an electron acceptor.

Inventive Example 10

Photopatterning Thiosulfate Polymer Composition Coating

To 1 ml of a 2 weight % solution of poly(vinyl benzyl thiosulfate sodium salt-co-methyl methacrylate-co-acrylic acid-co-N-butyl-N'-[2-(ethoxy-2-acrylate)ethyl]-1,4,5,8-naphthalenetetracarboxylic diimide) (prepared as described above in Inventive Example 4) in water, 1 ml of tetrahydrofuran was added and the thiosulfate polymer composition was spin-coated onto a glass plate substrate at 1000 rpm. The thiosulfate polymer coating was protected from UV and blue light at all times, and was then dried for 5 minutes on a hot plate at 50° C. The dried thiosulfate polymer composition coating was exposed to light using an Hg lamp through a mask for 6 seconds and then washed with water, followed by washing with acetone. The exposed areas of the thiosulfate polymer composition coating on the glass plate substrate were rendered insoluble forming an image of the mask, whereas non-crosslinked thiosulfate polymer composition in the unexposed areas of the dried coating was washed away.

These results show that the thiosulfate polymer compositions of the present invention can be used to prepare a photoresist useful for forming an image.

Inventive Example 11

Selective Area Deposition of a Metal on Photopatterned Thiosulfate Polymer Composition To 1 ml of an 11 weight % solution of poly(2-hydroxy-2-thiosulfate sodium salt ethyl methacrylate-co-methyl methacrylate) (prepared in Synthesis 4) in water, 2.2 mg of triphenylpyrrylium tetrafluoroborate salt of electron-accepting photosensitizer component PS-21, 370 mg of tetrabutylammonium chloride, and 1 ml of tetrahydrofuran were added and the solution was spin-coated on a glass plate substrate at 1000 rpm. The thiosulfate polymer coating was protected from UV and blue light at all times, and then dried for 5 minutes on a hot plate at 50° C. The dried thiosulfate polymer coating was exposed to light using an Hg lamp through a mask for 10 seconds and then washed with water, followed by washing with acetone. The exposed areas of the thiosulfate polymer composition coating on the glass plate substrate were rendered insoluble (crosslinked) forming an image of the mask, whereas the non-crosslinked thiosulfate polymer composition coating in the unexposed areas was washed away.

This patterned coating was covered with an aqueous solution of silver nitrate followed by an aqueous solution of ascorbic acid, and washing. Metallic silver was deposited on the photopatterned areas.

These results demonstrate that the thiosulfate polymer compositions of the present invention can be used to form a photoresist that can be used to form an image useful for selective deposition of silver metal.

Inventive Example 12

Selective Area Deposition of Metal Nanowires on Thiosulfate Polymer Composition

Silver nanowires were prepared using a standard polyol procedure as described in US Patent Application Publication 2011/0174190 (Sepa et al.), the disclosure of which is incorporated herein by reference.

Following three solutions were prepared:

Solution 1: A mixture of 6 grams of silver nitrate and 37 grams of propylene glycol in a beaker was stirred in the dark for about 6 hours. One half of Solution 1 was used for the initial and main additions. The other half of the solution was kept in the dark to be used for the final slow addition of silver nitrate during the second day of the reaction.

Solution 2: A mixture of 1.18 grams of tetrabutylammonium chloride was dissolved in 10.62 grams of propylene glycol.

Solution 3: In a 1 liter, three-neck flask, a mixture of 7.2 grams of poly(vinyl pyrrolidone) and 445 grams of propylene glycol was heated to about 90° C. Once the solution had stabilized at 90° C., it was purged with argon for 5 minutes. Then, 0.6% of Solution 1 was added into the reaction vessel and stirred for 10 seconds, followed by the addition of Solution 2. After 4 minutes of allowing the seed reaction to begin, 49.4% of Solution 1 was added to the reaction over the course of 45 seconds, and the reaction was maintained at about 90° C. for 15 hours. All of these steps were carried out in vessels that were wrapped with aluminum foil to prevent exposure to light. After 15 hours of heating, the remaining 50% of Solution 1 was added slowly over the course of 4 hours using a syringe pump. The reaction was allowed to continue for an additional hour at which point heating was stopped and 100 ml of deionized water were added.

The whole crude reaction solution was allowed to settle for about 4 days. The supernatant was silvery in color with a slight yellow tinge indicating a high concentration of Ag nanowires. The sediment was silvery without a yellow tinge. The sediment was re-suspended in deionized water and viewed at 100× magnification using an oil immersion lens optical microscope. The resulting images showed a large population of silver nanowires with some nanoparticles. The solution was then taken through a second settling process.

A thiosulfate polymer composition patterned coating was prepared in the following manner:

An 8 weight % solution of poly(vinyl benzyl thiosulfate sodium salt-co-methyl methacrylate-co-1,8-naphthalimido-hexyl acrylate) (prepared in Invention Example 4) in water was spin-coated on a polyethylene terephthalate substrate at 1000 rpm. The thiosulfate polymer coating was protected from UV and blue light at all times, and then dried for 5 minutes on a hot plate at 50° C., followed by exposure to light using the Hg lamp through a mask for 10 seconds, and the washed with water. The exposed areas of the dry thiosulfate polymer composition coating on the glass plate substrate were rendered insoluble (crosslinked) forming an image of the mask, whereas non-crosslinked thiosulfate polymer composition coating in the unexposed areas was washed away.

The patterned thiosulfate polymer composition coating was immersed in a 1 weight % solution of the silver nanowires in water for 1 minute and then thoroughly washed with water. High resolution images of the patterned thiosulfate polymer composition coating clearly showed selective absorption of silver nanowires only in the photopatterned areas.

These results demonstrate that the thiosulfate polymer compositions of the present invention can be used to form photoresists that can then be used to provide an image for selective deposition of silver nanowires.

Inventive Example 13

Formation of Conductive Patterned Coating Using Thiosulfate Polymer Composition Patterned Silver Wires A silver metalizing bath was made by combining two separate baths. One bath was a silver ion solution, while the other bath was a reducing agent solution. These two baths are denoted below them as Solutions A and B, respectively.

Solution A:

Silver nitrate (0.817 g) was dissolved in 0.64 ml of ammonium hydroxide and then diluted by addition of 10 ml distilled water.

Rochelle's Salt Solution B:

Sodium potassium tartrate (Rochelle's salt, 2.86 g) and 0.205 grams of magnesium sulfate were dissolved in 10 ml of distilled water.

Plating Method:

Samples were immersed in a mixture of Solution A and B for 1 to 5 minutes and subsequently washed with water.

Plating of Patterned Silver Nanowires:

The patterned coating of Inventive Example 12 was immersed in a silver plating solution for 2 minutes and then washed with water. Metallic silver pattern was formed. Surface resistivity of the patterned coating was measured to 10-15Ω/□ using a four-point probe.

Inventive Example 14

Imaging Thiosulfate Polymer Composition Coating

To 1 ml of an 8 weight % solution of poly(vinyl benzyl thiosulfate sodium salt-co-methyl methacrylate) (prepared as described in Synthesis 1) in water, various amounts in 1.6 mg of 4-phenyl-N-ethoxy pyridinium hexafluorophosphate of electron-accepting photosensitizer component PS-12, various amounts in grams of tetrabutylammonium chloride, and 1 ml of tetrahydrofuran was added and the resulting thiosulfate polymer composition was spin-coated on a glass plate substrate at 1000 rpm. The coated thiosulfate polymer composition was protected from UV and blue light at all times. The thiosulfate polymer composition coating was dried for 5 minutes on a hot plate at 50° C. The resulting article was exposed to light using a mercury lamp through a mask for 10 seconds and then washed with water, followed by washing with acetone. The exposed regions of the thiosulfate polymer composition coating on glass plate were rendered insoluble (crosslinked), forming an image of the mask, whereas non-crosslinked thiosulfate polymer composition in the non-exposed regions of the thiosulfate polymer composition coating was washed away.

The results from these experiments demonstrate that the thiosulfate polymer compositions of this invention can be used to provide articles that can be used to provide photoresists.

Inventive Example 15

Imaging Thiosulfate Polymer Containing Photosensitizer

To 1 ml of a 2 weight % solution of poly(vinyl benzyl thiosulfate sodium salt-co-methyl methacrylate-co-acrylic acid-co-N-butyl-N'-[2-(ethoxy-2-acrylate)ethyl]-1,4,5,8-naphthalenetetracarboxylic diimide) (prepared in Inventive Example 2) in water, was added 1 ml of tetrahydrofuran. The resulting thiosulfate polymer composition was spin-coated onto a glass plate substrate at 1000 rpm. The thiosulfate polymer composition coating was protected from UV and blue light at all times. The thiosulfate polymer composition coating was dried for 5 minutes on a hot plate at 50° C. The thiosulfate polymer composition coating was exposed to light using a mercury lamp through a mask for 6 seconds and was then washed with water, followed by washing with acetone. The exposed regions of the dry thiosulfate polymer composition coating on glass plate substrate were rendered insoluble (crosslinked) forming an image of the mask, whereas the dry non-crosslinked thiosulfate polymer composition in non-exposed regions was washed away.

These results demonstrate that the thiosulfate polymer composition of the present invention can be used to form an article that can be imaged to form a photoresist.

Inventive Example 16

Selective Area Deposition of Silver Metal on Imaged Thiosulfate Polymer Composition To 1 ml of an 8 weight % solution of polyvinyl benzyl thiosulfate sodium salt-co-methyl methacrylate) (prepared as described above in Synthesis 1) in water, were added 1.6 mg of 4-phenyl-N-ethoxy pyridinium hexafluorophosphate of electron-accepting photosensitizer component PS-12, 250 mg of tetrabutylammonium chloride, and 1 ml of tetrahydrofuran. The resulting thiosulfate polymer composition was then spin-coated onto a glass plate substrate at 100 rpm. The thiosulfate polymer composition coating was protected from UV and blue light at all times. The thiosulfate polymer composition coating was dried for 5 minutes on a hot plate at 50° C. The dried thiosulfate polymer composition coating was then exposed to light using a mercury lamp through a mask for 10 seconds and was then washed with water, followed by washing with acetone. The exposed regions of the dry thiosulfate polymer composition coating on the glass plate substrate were rendered insoluble (crosslinked), forming an image, whereas the non-crosslinked thiosulfate polymer composition in the non-exposed regions was washed away.

The resulting pattern in the thiosulfate polymer composition layer was covered with an aqueous solution of silver nitrate followed by an aqueous solution of ascorbic acid, followed by washing. Metallic silver was deposited on the patterned regions of the thiosulfate polymer composition.

This example demonstrates that the thiosulfate polymer compositions of the present invention can be used to form articles that can be used to provide a photoresist that can be used for selective deposition of silver metal.

Inventive Example 17

Surface Energy Modulation using Thiosulfate Polymer Composition

To 1 ml of a 10 weight % solution of poly(vinyl benzyl thiosulfate sodium salt-co-methyl methacrylate) (prepared as described above in Synthesis 1) in water, 2.2 mg of electron-accepting photosensitizer component PS-22, 100 mg of tetrabutylammonium chloride, and 1 ml of tetrahydrofuran were added and the resulting solution was spin-coated onto a glass plate substrate at 1000 rpm and then dried for 5 minutes on a hot plate at 50° C. The thiosulfate polymer composition coating was protected from UV and blue light at all times. The dried thiosulfate polymer composition coating was then exposed to light using a mercury lamp for 100 seconds and then quickly rinsed with water and dried. The exposed regions of the dry thiosulfate polymer composition coating on the glass plate substrate were rendered insoluble from crosslinking of the thiosulfate polymer.

The water contact angle was measured before (45°) and after Irradiation (65°)using a KRUSS contact angle measurement system. This example demonstrates that the thiosulfate polymer compositions of the present invention can be used for photochemical variation of surface energy of a coating or substrate.

The invention has been described in detail with particular reference to certain preferred embodiments thereof, but it will be understood that variations and modifications can be effected within the spirit and scope of the invention.

The invention claimed is:

1. A composition comprising a non-crosslinked thiosulfate polymer comprising a polymer backbone and thiosulfate groups distributed along the polymer backbone, and an electron-accepting photosensitizer component, wherein the composition has photosensitivity to actinic radiation at a wavelength of at least 200 and up to and less than 725 nm sufficient to cause crosslinking of the thiosulfate groups to form disulfide bonds, wherein the electron-accepting photosensitizer component satisfies the following Equation 3:

$$E_{PS*} + E_{PS}^{red} > E_R^{ox}$$

wherein $E_{PS*}$ represents the excitation energy of the electron-accepting photosensitizer component, $E_{PS}^{red}$ represents the reduction potential of the electron-accepting photosensitizer component, and $E_R^{ox}$ is the oxidation potential of the thiosulfate group in the non-crosslinked thiosulfate polymer, and the electron-accepting photosensitizer component is a thiazolium salt, a pyrylium salt, a naphthalene diimide, a naphthalene imide, a cyano-substituted carbocyclic aromatic compound, an aromatic anhydride, an aromatic imide, a condensed pyridinium salt, a quinone, or a ketocoumarin.

2. The composition of claim 1, wherein the electron-accepting photosensitizer component is a covalently-connected component of the non-crosslinked thiosulfate polymer.

3. The composition of claim 2, wherein the non-crosslinked thiosulfate polymer is a copolymer comprising, in random order: (a) recurring units comprising thiosulfate groups, and (b) recurring units comprising the electron-accepting photosensitizer component.

4. The composition of claim 3, wherein the copolymer comprises, in random order, (c) recurring units other than the (a) and (b) recurring units, which (c) recurring units comprise a pendant negative-charged or positive-charged group, the (c) recurring units being present in an amount of at least 0.1 mol %, based on the total recurring units in the copolymer.

5. The composition of claim 4, wherein the (c) recurring units comprise a pendant carboxy, carboxylate, phospho, phosphonate, phosphate, sulfo, sulfonate, or sulfite group.

6. The composition of claim 4, wherein the (c) recurring units are present in an amount of at least 0.1 mol % up to and including 50 mol %.

7. The composition of claim 4, wherein the (c) recurring units are present in the copolymer in an amount of up to 50 mol %, the (a) recurring units are present in the copolymer in an amount of at least 1 mol %, and the copolymer further comprises (d) recurring units that have a total neutral charge and are present in an amount of at least 1 mol % and up to and including 49 mol %.

8. The composition of claim 1, comprising (a) recurring units comprising thiosulfate groups and (c) recurring units that comprise a pendant negative-charged or positive-charged group in an amount of at least 0.1 mol %.

9. The composition of claim 7, wherein the molar ratio of the (a) recurring units to the (d) recurring units is from 1:3 to 3:1.

10. The composition of claim 1, wherein the electron-accepting photosensitizer component is present in an amount of at least 0.1 mol % and up to and including 10 mol %, in relation to the molar amount of thiosulfate groups present in the composition.

11. The composition of claim 1, wherein the electron-accepting photosensitizer component is a compound separate from the non-crosslinked thiosulfate polymer.

12. The composition of claim 1, wherein the electron-accepting photosensitizer component is an organic photosensitizer N-containing heterocyclic compound.

13. A composition comprising a non-crosslinked thiosulfate polymer comprising a polymer backbone and thiosulfate groups distributed along the polymer backbone, and an electron-accepting photosensitizer component, wherein the composition has photosensitivity to actinic radiation at a wavelength of at least 200 and up to and less than 725 nm sufficient to cause crosslinking of the thiosulfate groups to form disulfide bonds, wherein the electron-accepting photosensitizer component satisfies the following Equation 3:

$$E_{PS*}+E_{PS}^{red}>E_{R}^{ox}$$

wherein $E_{PS*}$ represents the excitation energy of the electron-accepting photosensitizer component, $E_{PS}^{red}$ represents the reduction potential of the electron-accepting photosensitizer component, and $E_{R}^{ox}$ is the oxidation potential of the thiosulfate group in the non-crosslinked thiosulfate polymer, wherein the electron-accepting photosensitizer component is an inorganic salt or complex.

14. The composition of claim 1 further comprising a complexing metal ion.

15. The composition of claim 1, further comprising tetraalkyl ammonium ions.

16. An article comprising a substrate having disposed thereon a coating comprising the composition of claim 1.

17. The article of claim 16, wherein the coating is provided as a pattern on the substrate.

18. A composition comprising a non-crosslinked thiosulfate polymer comprising a polymer backbone and thiosulfate groups distributed along the polymer backbone, and an electron-accepting photosensitizer component, wherein the composition has photosensitivity to actinic radiation at a wavelength of at least 200 and up to and less than 725 nm sufficient to cause crosslinking of the thiosulfate groups to form disulfide bonds, wherein the electron-accepting photosensitizer component is one of the following compounds PS-1 through PS-11 and PS-15 through PS-28:

PS-1
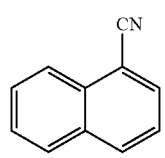

PS-2
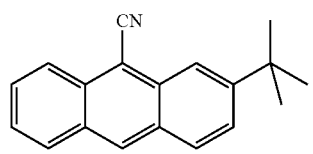

PS-3
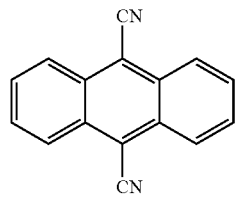

PS-4
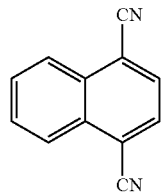

PS-5
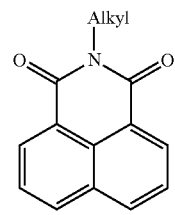

PS-6
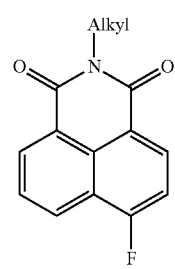

PS-7
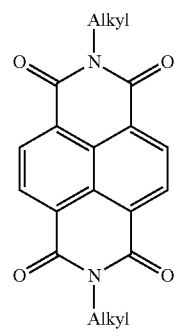

PS-8
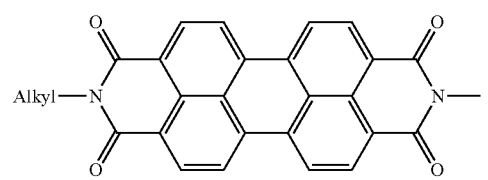

PS-9
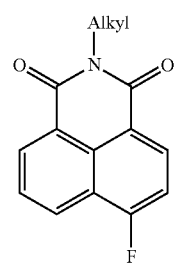

PS-10
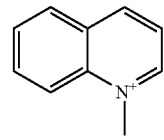

-continued
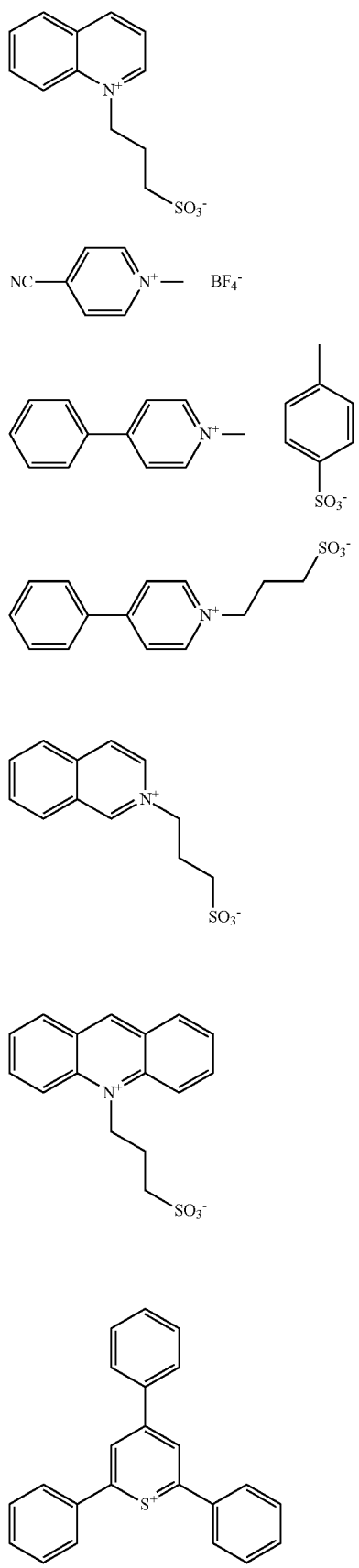
PS-15
PS-16
PS-17
PS-18
PS-19
PS-20
-continued
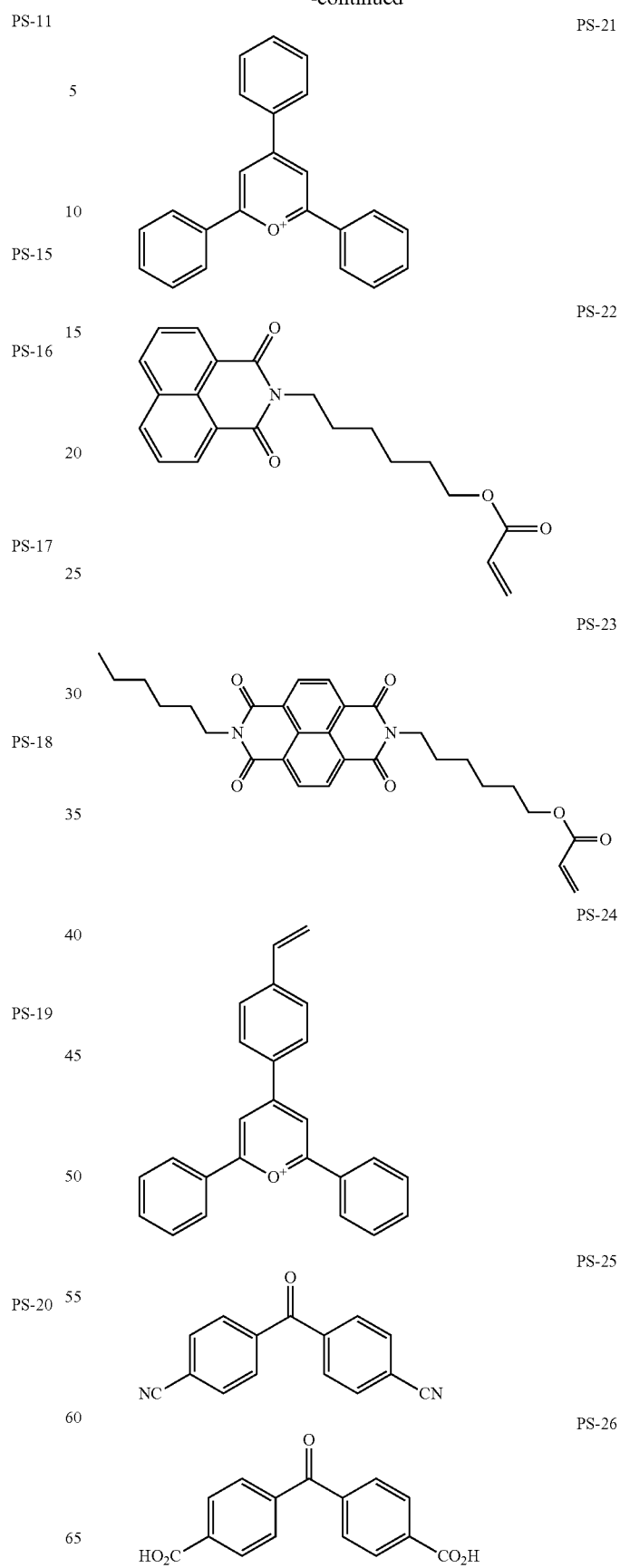
PS-11
PS-21
PS-22
PS-23
PS-24
PS-25
PS-26

-continued
PS-27
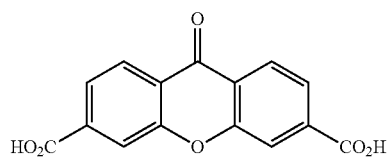
PS-28
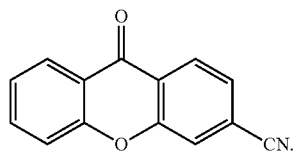
* * * * *